US012637475B2

(12) United States Patent
Itami et al.

(10) Patent No.: US 12,637,475 B2

(45) Date of Patent: May 26, 2026

(54) METHOD FOR PRODUCING NAPHTHYLSILOLE, NAPHTHYLSILOLE CONTAINING HETEROCYCLIC GROUP, AND GRAPHENE NANORIBBON CONTAINING HETEROCYCLIC GROUP

(71) Applicants: National University Corporation Tokai National Higher Education and Research System, Nagoya (JP); Taoka Chemical Co., Ltd., Osaka (JP)

(72) Inventors: Kenichiro Itami, Nagoya (JP); Hideto Ito, Nagoya (JP); Kaho Matsushima, Nagoya (JP); Kazuo Murakami, Osaka (JP); Hidefumi Nakatsuji, Osaka (JP); Shunsuke Ishida, Osaka (JP)

(73) Assignees: National University Corporation Tokai National Higher Education and Research System, Nagoya (JP); Taoka Chemical Co., Ltd., Osaka (JP)

( * ) Notice: Subject to any disclaimer, the term of this patent is extended or adjusted under 35 U.S.C. 154(b) by 698 days.

(21) Appl. No.: 17/909,317

(22) PCT Filed: Feb. 25, 2021

(86) PCT No.: PCT/JP2021/007201

§ 371 (c)(1),
(2) Date: Oct. 6, 2022

(87) PCT Pub. No.: WO2021/177144

PCT Pub. Date: Sep. 10, 2021

(65) Prior Publication Data

US 2023/0121865 A1 Apr. 20, 2023

(30) Foreign Application Priority Data

Mar. 4, 2020 (JP) ................................ 2020-036821

(51) Int. Cl.

| | |
|---|---|
| ***C07D 495/14*** | (2006.01) |
| ***C07C 17/26*** | (2006.01) |
| ***C07C 25/22*** | (2006.01) |
| ***C07C 309/65*** | (2006.01) |
| ***C07D 333/12*** | (2006.01) |
| ***C07F 7/08*** | (2006.01) |

(52) U.S. Cl.

CPC ............ *C07D 495/14* (2013.01); *C07C 17/26* (2013.01); *C07C 25/22* (2013.01); *C07C 309/65* (2013.01); *C07D 333/12* (2013.01); *C07F 7/0816* (2013.01)

(58) Field of Classification Search

CPC .................................................. C07D 495/14

See application file for complete search history.

(56) References Cited

U.S. PATENT DOCUMENTS

| | | | |
|---|---|---|---|
| 9,556,085 | B2 | 1/2017 | Dichtel et al. |
| 10,329,378 | B2 | 6/2019 | Schwab et al. |
| 2010/0187512 | A1 | 7/2010 | Ito |

(Continued)

FOREIGN PATENT DOCUMENTS

| | | | |
|---|---|---|---|
| CN | 103635423 | A | 3/2014 |
| CN | 106103392 | A | 11/2016 |
| CN | 106543215 | A | 3/2017 |
| CN | 106660803 | A | 5/2017 |
| CN | 107652287 | A | 2/2018 |
| CN | 110204691 | A | 9/2019 |

(Continued)

OTHER PUBLICATIONS

Van der Boon, Leon J., et al. "Toward Asymmetric Synthesis of Pentaorganosilicates." Topics in Catalysis. (2018), vol. 61, pp. 674-684. (Year: 2018).*

(Continued)

*Primary Examiner* — John S Kenyon

(74) *Attorney, Agent, or Firm* — Leydig, Voit & Mayer, Ltd.

(57) ABSTRACT

Provided is a method that allows for a safer production of a naphthylsilole for use as a starting material for GNR, which involves reacting a compound of formula (1):

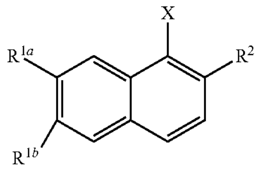

(1)

(wherein $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ are optionally bound to each other to form a ring; $R^2$ represents an aromatic hydrocarbon ring or a heterocyclic ring; and X represents a bromine or iodine atom) with a lanthanide- and lithium-containing ate complex to produce a lanthanide complex of the compound of formula (1); and then reacting it with a silyl compound of formula (2):

$R^{3a}R^{3b}SiCl_2$ (2)

(wherein $R^{3a}$ and $R^{3b}$ are the same or different and represent an optionally branched $C_1$-$C_4$ alkyl group or a phenyl group).

4 Claims, No Drawings

(56) References Cited

U.S. PATENT DOCUMENTS

| | | | |
|---|---|---|---|
| 2014/0212668 A1 | 7/2014 | Dichtel et al. |
| 2015/0325799 A1 | 11/2015 | Hwang et al. |
| 2017/0051101 A1 | 2/2017 | Schwab et al. |
| 2017/0081192 A1 | 3/2017 | Schwab et al. |
| 2017/0141331 A1 | 5/2017 | Kim et al. |
| 2018/0053902 A1 | 2/2018 | Kim et al. |
| 2022/0006012 A1 | 1/2022 | Hatakeyama et al. |

FOREIGN PATENT DOCUMENTS

| | | | |
|---|---|---|---|
| EP | 3940013 | A1 | 1/2022 |
| JP | 2014-019671 | A | 2/2014 |
| JP | 2014-019679 | A | 2/2014 |
| JP | 2018-172237 | A | 11/2018 |
| JP | 2021-011471 | A | 2/2021 |
| KR | 10-2010-0064712 | A | 6/2010 |
| KR | 10-2015-0042386 | A | 4/2015 |
| KR | 10-2016-0076931 | A | 7/2016 |
| WO | WO 2008/156052 | A1 | 12/2008 |
| WO | WO 2010/038956 | A2 | 4/2010 |
| WO | WO 2010/064871 | A1 | 6/2010 |
| WO | WO 2012/083171 | A1 | 6/2012 |
| WO | WO 2014/126241 | A1 | 8/2014 |
| WO | WO 2017/131190 | A1 | 8/2017 |
| WO | WO 2019/102936 | A1 | 5/2019 |
| WO | WO 2020/184625 | A1 | 9/2020 |

OTHER PUBLICATIONS

American Chemical Society. Chemical Abstract Service. RN 1876412-60-0. Entered into STN: Feb. 29, 2016. (Year: 2016).*

American Chemical Society. Chemical Abstract Service. RN 219-25-0. Entered into STN: Nov. 16, 1984. (Year: 1984).*

Daigle, Maxime, et al. "Regioselective Synthesis of Nanographenes by Photochemical Cyclodehydrochlorination." Angiew. Chem. Int. Ed. (2016), vol. 55, pp. 2042-2047. (Year: 2016).*

China National Intellectual Property Administration, Office Action in Chinese Patent Application No. 202180018018.2 (Apr. 12, 2024).

Barluenga et al., "The Reaction of o-Alkynylarene and Heteroarene Carboxaldehyde Derivatives with Iodonium lons and Nucleophiles: A Versatile and Regioselective Synthesis of 1H-Isochromene, Naphthalene, Indole, Benzofuran, and Benzothiophene Compounds," *Chem. Eur. J.*, 12(22): 5790-5805 (2006).

Dong et al., "Pd(OAc)$_2$-Catalyzed Domino Reactions of 1,2-Dihaloarenes and 2-Haloaryl Arenesulfonates with Grignard Reagents: Efficient Synthesis of Substituted Fluorenes," *Tetrahedron.*, 64(11): 2537-2552 (2008).

Kamikawa et al., "Control of Reactive Site in Palladium-Catalyzed Grignard Cross-Coupling of Arenes Containing both Bromide and Triflate," *Tetrahedron Letters*, 38(40): 7087-7090 (1997).

McConachie et al., "A Novel Base-Induced Cyclization of Selected Benzyl Alkynyl Sulfides for the Synthesis of 2-Aryl-2, 3-Dihydrothiophenes," *Tetrahedron Letters*, 41(30): 5637-5641 (2000).

Mochida et al., "Palladium-Catalyzed Intramolecular Coupling of 2-[(2-Pyrrolyl)silyl]aryl Triflates through 1,2-Silicon Migration," *J. Am. Chem. Soc.*, 131(24): 8350-8351 (2009).

Wei et al., "Preparation of Polyfunctional Biaryl Derivatives by Cyclolanthanation of 2-Bromobiaryls and Heterocyclic Analogues Using nBu2LaCl•4 LiCl," *Angew. Chem. Int. Ed.*, 58(44): 15631-15635 (2019).

Japan Patent Office, International Search Report in International Patent Application No. PCT/JP2021/007201 (Apr. 13, 2021).

Yano et al., "Living Annulative π-extension Polymerization for Graphene Nanoribbon Synthesis ," *Nature*, 571: 387-392 and Supplementary Information (2019).

Yano et al., "Retraction Note: Living Annulative π-extension Polymerization for Graphene Nanoribbon Synthesis ," *Nature*, 588(7836): 180 (2020).

European Patent Office, Extended European Search Report in European Patent Application No. 21765159.5 (Mar. 22, 2024).

* cited by examiner

METHOD FOR PRODUCING NAPHTHYLSILOLE, NAPHTHYLSILOLE CONTAINING HETEROCYCLIC GROUP, AND GRAPHENE NANORIBBON CONTAINING HETEROCYCLIC GROUP

TECHNICAL FIELD

The present invention relates to a method for producing a naphthylsilole that is for use as a starting material for a graphene nanoribbon (hereinafter sometimes referred to as "GNR").

BACKGROUND ART

Graphene nanoribbons (GNRs) are materials that are expected to find application in semiconductors, solar batteries, transparent electrodes, high-speed transistors, organic EL devices, and the like. Methods for producing GNRs are roughly classified into two methods: the top-down method and the bottom-up method. The latter method, i.e., the bottom-up method, is particularly attractive in terms of its ability to synthesize a large amount of GNRs with precise control of the edge structure and width thereof.

The present inventors focused their attention on the production of GNRs by the bottom-up method, and performed extensive research on the method for producing GNRs. As a result, the inventors found a production method using a naphthylsilole as a starting material as a method for producing GNRs with fewer steps, while suppressing side reactions (Patent Literature (PTL) 1).

CITATION LIST

Patent Literature

PTL 1: WO2020/184625

SUMMARY OF INVENTION

Technical Problem

PTL 1 mentioned above discloses that a naphthylsilole, a starting material for GNR, can be produced, for example, by a method comprising reacting a compound represented by formula (9):

(9)

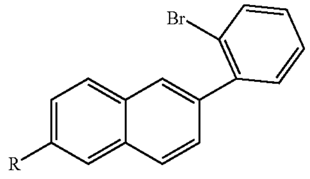

(wherein R represents a substituent)

with n-butyl lithium (n-BuLi) and then reacting the resulting compound with dimethylsilyl chloride to obtain a silyl compound represented by formula (10):

(10)

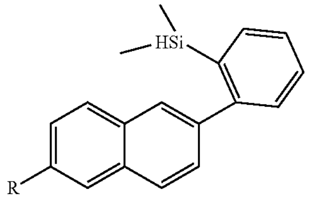

(wherein R is as defined above), and cyclizing the silyl compound using di-tert-butylperoxide ($(t\text{-BuO})_2$) (Synthesis Example 2 of PTL 1). However, this production method must use dimethylsilyl chloride, which has a very low flash point and a very low boiling point; and also must use di-tert-butylperoxide, which is a self-reactive organic peroxide. Therefore, in the industrial implementation thereof, this production method is not considered to be fully safe in terms of disaster prevention.

An object of the present invention is to provide a method for more safely producing a naphthylsilole for use as a starting material for GNR.

Solution to Problem

The present inventors conducted extensive research to solve the above problem. As a result, the inventors found that the following method is capable of producing a naphthylsilole more safely from a relatively low-risk compound. More specifically, the present invention includes the following inventions.

Item 1. A method for producing a compound represented by formula (3):

(3)

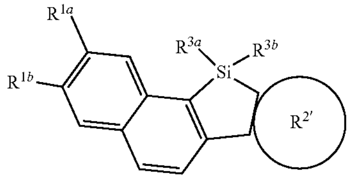

(wherein $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ are optionally bound to each other to form a ring; $R^{2'}$ represents an aromatic hydrocarbon ring or a heterocyclic ring; $R^{3a}$ and $R^{3b}$ are the same or different and represent an optionally branched $C_1$-$C_4$ alkyl group or a phenyl group);

the method comprising the following steps in this order:

a step of reacting a compound represented by formula (1)

(1)

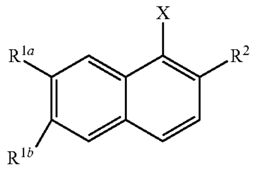

(wherein $R^{1a}$ and $R^{1b}$ are as defined above; $R^2$ represents an aromatic hydrocarbon group or a heterocyclic group; and X represents a bromine atom or an iodine atom)

with a lanthanide- and lithium-containing ate complex to produce a lanthanide complex of the compound represented by formula (1); and a step of reacting the lanthanide complex with a silyl compound represented by formula (2):

$R^{3a}R^{3b}SiCl_2$ (2)

(wherein $R^{3a}$ and $R^{3b}$ are as defined above).

Item 2. A compound represented by formula (1):

(1)

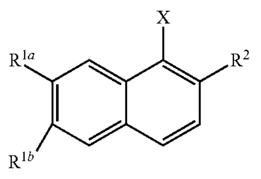

(wherein $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ are optionally bound to each other to form a ring; $R^2$ represents an aromatic hydrocarbon group or a heterocyclic group; and X represents a bromine atom or an iodine atom).

Item 3. A method for producing the compound of Item 2, comprising reacting a compound represented by formula (4):

(4)

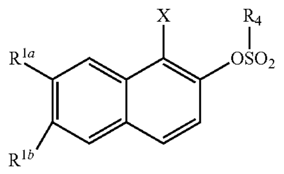

(wherein $R^{1a}$, $R^{1b}$, and X are as defined above; $R^4$ represents an optionally branched $C_1$-$C_4$ alkyl group, an optionally branched $C_1$-$C_4$ halogenated alkyl group, or an aromatic hydrocarbon group) with a compound represented by formula (5)

$R^2MgBr$ (5)

(wherein $R^2$ is as defined above).

Item 4. A compound represented by formula (4):

(4)

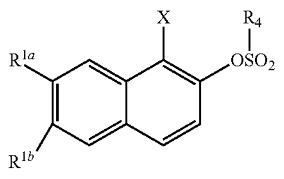

(wherein $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ are optionally bound to each other to form a ring; $R^4$ represents an optionally branched $C_1$-$C_4$ alkyl group, an optionally branched $C_1$-$C_4$ halogenated alkyl group, or an aromatic hydrocarbon group; and X represents a bromine atom or an iodine atom).

Item 5. A compound comprising at least one structural unit represented by formula (3a):

(3a)

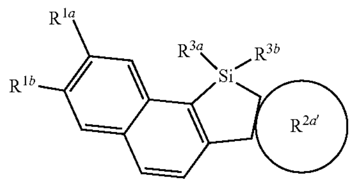

(wherein $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ are optionally bound to each other to form a ring; $R^{2a'}$ represents a heteroaromatic ring; $R^{3a}$ and $R^{3b}$ are the same or different and represent an optionally branched $C_1$-$C_4$ alkyl group or a phenyl group).

Item 6. A graphene nanoribbon comprising at least one structural unit represented by formula (6):

(6)

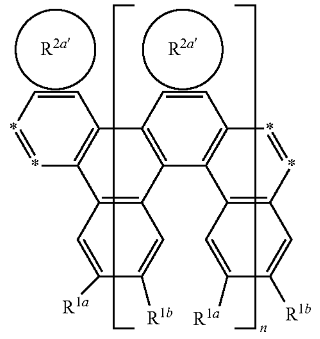

(wherein * represents a bonding point; n represents an integer of 0 or more; $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ bound to the same benzene ring are optionally bound to each other to form a ring; and $R^{2a'}$ represents a heteroaromatic ring).

Item 7. The graphene nanoribbon according to Item 6 comprising at least one structural unit represented by formula (7):

(7)

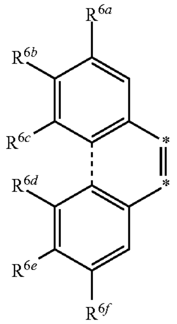

(wherein the dotted line represents no bond or a single bond; * represents a bonding point; $R^{6a}$, $R^{6b}$, $R^{6c}$, $R^{6d}$, $R^{6e}$, and $R^{6f}$ are the same or different and represent a hydrogen atom, a halogen atom, an alkyl group, a cycloalkyl group, a (poly) ether group, an ester group, a boronic acid group or an ester group of boronic acid, an aromatic hydrocarbon group, or a heterocyclic group; and $R^{6c}$ and $R^{6d}$ are optionally bound to each other to form a ring).

Item 8. The graphene nanoribbon according to Item 6 or 7 comprising at least one structural unit represented by formula (8):

(8)

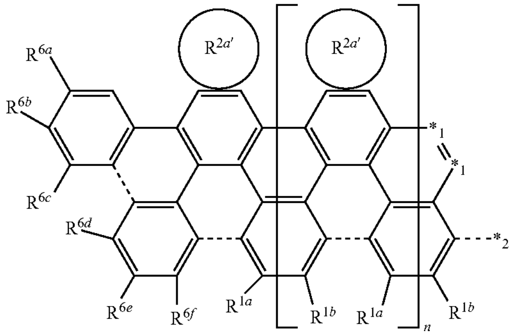

(wherein the dotted lines are the same or different and represent no bond or a single bond; *1 represents a bonding point; *2 represents a bonding point when the dotted line connecting to *2 is a single bond; n represents an integer of 0 or more; $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ bound to the same benzene ring are optionally bound to each other to form a ring; $R^{2a'}$ represents a heteroaromatic ring; $R^{6a}$, $R^{6b}$, $R^{6c}$, $R^{6d}$, $R^{6e}$, and $R^{6f}$ are the same or different and represent a hydrogen atom, a halogen atom, an alkyl group, a cycloalkyl group, a (poly)ether group, an ester group, a boronic acid group or an ester group of boronic acid, an aromatic hydrocarbon group, or a heterocyclic group; and $R^{6c}$ and $R^{6d}$ are optionally bound to each other to form a ring).

Advantageous Effects of Invention

The present invention makes it possible to produce a naphthylsilole without using compounds having a very low flash point and a very high boiling point or self-reactive organic peroxide. Since naphthylsilole can be produced by a one-pot process from a compound represented by formula (1), the naphthylsilole can be produced more conveniently than the known production methods described above.

Further, the present invention can provide an innovative method for producing a compound represented by formula (1). Specifically, according to the production method discovered by the present inventors, that is, a novel production method comprising reacting a compound represented by formula (4) with arylmagnesium bromide represented by formula (5), since the sulfonyl moiety of the compound represented by formula (4) is selectively reacted with arylmagnesium bromide represented by formula (5), it is unnecessary to introduce a bromine or iodine atom after the coupling reaction when a compound represented by formula (1) is to be produced. This enables the production of the compound represented by formula (1) having various structures and also allows the provision of a high-purity compound represented by formula (1) at lower cost. Thus, the method for producing the naphthylsilole of the present invention is capable of producing a naphthylsilole that is useful not only as a starting material for GNR but also as a starting material monomer for products other than GNR (e.g., monomers for organic EL devices, organic semiconductors, organic thin-film solar cells, etc.), and that has a structure that cannot be produced by heretofore known methods.

Typical examples of naphthylsiloles having a structure that cannot be produced by heretofore known methods include naphthylsiloles with a heteroaromatic ring that have a structure represented by formula (3a). Since the polymerization of naphthylsilole having a heteroaromatic ring under the conditions described in PTL 1 (APEX polymerization) can produce GNRs having a heteroaromatic ring (specifically GNRs having a structural unit represented by formula (6), (7), or (8)), GNRs having properties different from those of heretofore known GNRs (specifically, GNRs with improved properties, in terms of ability to accept electrons or holes, redox response, and ability to transport charge through precise control of the band gap) can be provided. Such GNRs having a heteroaromatic ring are especially useful for light-emitting materials, organic semiconductors, conductive materials, etc.

DESCRIPTION OF EMBODIMENTS

In the present specification, the terms "comprise" and "contain" include the concepts of "comprise," "consist essentially of," and "consist of." Further, in the present specification, the numerical range represented by "A to B" means A or more and B or less.

(1-1) Method for Producing the Naphthylsilole of the Present Invention

As shown in the following reaction scheme, the method for producing a naphthylsilole represented by formula (3) of the present invention comprises the following steps, in this order:

- a step of reacting a compound represented by formula (4) with arylmagnesium bromide represented by formula (5) to obtain a compound represented by formula (1) (step 1); and
- a step of reacting the compound represented by formula (1) with a lanthanide- and lithium-containing ate complex to produce a lanthanide complex of the compound represented by formula (1) in the reaction system, and reacting the lanthanide complex with a silyl compound represented by formula (2) (step (2)).

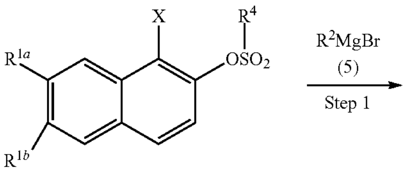

(4)

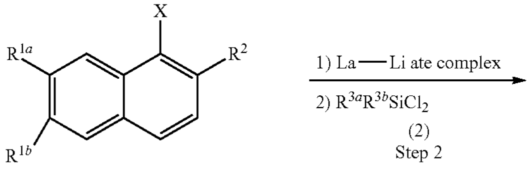

(1)

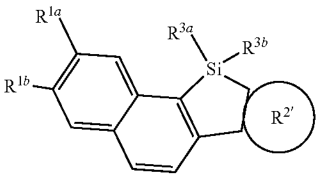

(3)

(wherein $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ are optionally bound to each other to form a ring; $R^2$ represents an aromatic hydrocarbon group or a heterocyclic group; $R^{2'}$ represents an aromatic hydrocarbon ring or a heterocyclic ring; $R^{3a}$ and $R^{3b}$ are the same or different and represent an optionally branched $C_1$-$C_4$ alkyl group or a phenyl group; X represents a bromine atom or an iodine atom; and $R^4$ represents an optionally branched $C_1$-$C_4$ alkyl group, an optionally branched $C_1$-$C_4$ halogenated alkyl group, or an aromatic hydrocarbon group).

Each compound and each step described above are described below in detail.

(1-1-1) Compounds Represented by Formulas (1) to (5)

Examples of the alkyl group represented by $R^{1a}$ and $R^{1b}$ in formula (4) include linear or branched $C_1$-$C_{20}$ (preferably $C_1$-$C_{15}$, and more preferably $C_1$-$C_{13}$) alkyl groups. Specific examples include methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, n-heptyl, n-octyl, n-nonyl, and n-decyl.

The alkyl group is substituted or unsubstituted. When the alkyl group is substituted, the substituent is not particularly limited and examples include halogen atoms, such as fluorine, chlorine, and bromine. When the alkyl group is substituted with at least one substituent, the number of substituents is not particularly limited and can be, for example, 1 to 3.

Preferable examples of the cycloalkyl group represented by $R^{1a}$ and $R^{1b}$ in formula (4) include $C_3$-$C_{20}$ (preferably $C_4$-$C_{15}$, and more preferably $C_5$-$C_{13}$) cycloalkyl groups. Specific examples include cyclopropyl, cyclobutyl, cyclopentyl, cyclohexyl, cycloheptyl, cyclooctyl, cyclononyl, and cyclodecyl.

The cycloalkyl group is substituted or unsubstituted. When the cycloalkyl group is substituted, the substituent is not particularly limited and examples include halogen atoms, such as fluorine, chlorine, and bromine; and $C_1$-$C_{20}$ hydrocarbon groups (such as methyl, ethyl, and n-propyl). When the cycloalkyl group is substituted with at least one substituents, the number of substituents is not particularly limited and can be, for example, 1 to 3.

The (poly)ether group represented by $R^{1a}$ and $R^{1b}$ in formula (4) refers to an ether group or a polyether group. Examples of ether groups include groups represented by $—OR^{11c}$(wherein $R^{11c}$ represents an alkyl group mentioned above). Preferably, $R^{11c}$ is an ether group having a $C_1$-$C_4$ alkyl group. Examples of polyether groups include groups represented by $—(OR^{11a})_k—OR^{11b}$ (wherein $R^{11a}$ and $R^{11b}$ are the same or different and represent an alkyl group; and k represents an integer of 1 to 20). The repeating units $OR^{11a}$ may be composed of the same repeating unit, or may include two or more different repeating units. Preferably, a polyether group wherein $R^{11a}$ and $R^{11b}$ each independently represent a $C_1$-$C_4$ alkyl group can be preferably used.

$R^{11a}$ and $R^{11b}$ are both an alkyl group, and examples of the alkyl group include those mentioned above. When the alkyl group has at least one substituent, the type and number of substituents can be the same as those mentioned above. k is preferably an integer of 1 to 20, more preferably an integer of 1 to 15, and even more preferably an integer of 1 to 5.

Examples of such polyether groups include $—(OC_2H_5)_2OCH_3$, $—(OC_2H_5)_3OCH_3$, $—(OC_2H_5)_4OCH_3$, $—(OC_2H_5)_{11}OCH_3$, $—(OC_2H_5)_{12}OCH_3$, and $(OC_2H_5)_{13}OCH_3$.

Examples of the ester group represented by $R^{1a}$ and $R^{1b}$ in formula (4) include groups represented by $—COOR^{11d}$ (wherein $R^{11d}$ represents an alkyl group mentioned above). An ester group wherein $R^{11d}$ is a $C_1$-$C_4$ alkyl group can be preferably used.

Specific examples of the halogen atom represented by $R^{1a}$ and $R^{1b}$ include fluorine, chlorine, bromine, and iodine.

The aromatic hydrocarbon group represented by $R^{1a}$ and $R^{1b}$ in formula (4) refers to groups having an aromatic hydrocarbon ring. At least one of the hydrogen atoms bound to carbon atoms on the aromatic heterocyclic ring is optionally replaced by a substituent.

Examples of the aromatic hydrocarbon ring of the aromatic hydrocarbon group include not only benzene rings, but also a ring obtained by fusing a plurality of benzene rings (fused benzene ring) and a ring obtained by fusing a benzene ring and another aromatic hydrocarbon ring (hereinafter, the ring obtained by fusing a plurality of benzene rings, and the ring obtained by fusing a benzene ring and another ring are also collectively referred to as "fused hydrocarbon rings"). Examples of the fused hydrocarbon rings include pentalene, indene, naphthalene, dihydronaphthalene, anthracene, tetracene, pentacene, pyrene, perylene, triphenylene, azulene, heptarene, biphenylene, indacene, acenaphthylene, fluorene, phenylene, and phenanthrene rings.

When at least one of the hydrogen atoms on the aromatic hydrocarbon ring of the aromatic hydrocarbon group is replaced by at least one substituent, the substituent is not particularly limited. Examples of substituents include halogens such as fluorine, chlorine, and bromine atoms; and $C_1$-$C_{20}$ hydrocarbon groups (e.g., methyl, ethyl, and n-propyl). When at least one of the hydrogen atoms on the aromatic hydrocarbon ring is replaced by at least one substituent, the number of substituents is not particularly limited and can be, for example, 1 to 3.

The heterocyclic group represented by $R^{1a}$ and $R^{1b}$ in formula (4) refers to groups having a heterocyclic ring (a substituent). The heterocyclic group may be a derivative group wherein at least one of the hydrogen atoms bound to carbon atoms on the heterocyclic ring is replaced by at least one functional group.

Examples of the heterocyclic ring of the heterocyclic group include heterocyclic rings containing at least one atom selected from the group consisting of nitrogen, oxygen, boron, phosphorus, silicon, and sulfur atoms (specifically heteroaromatic or heteroaliphatic rings, and particularly heteroaromatic rings). Specific examples of the heterocyclic ring include heteroaromatic rings, such as furan, thiophene, pyrrole, silole, borol, phosphole, oxazole, dioxole, thiazole, pyridine, pyridazine, pyrimidine, and pyrazine rings. Examples further include heterocyclic fused rings of these rings, heterocyclic fused rings of these rings and benzene rings, and heterocyclic fused rings of these rings and fused hydrocarbon rings (e.g., thienothiophene, quinoline, and benzodioxole rings).

When at least one of the hydrogen atoms on the heterocyclic ring of the heterocyclic group is replaced by at least one substituent, the substituent is not particularly limited and examples include halogens such as hydrogen, chlorine, and bromine atoms; and $C_1$-$C_{20}$ hydrocarbon groups (e.g., methyl, ethyl, and n-propyl). However, the substituent is not limited thereto and any substituents can be used. When at least one of the hydrogen atoms on the heterocyclic ring of the heterocyclic group is replaced by at least one substituent, the number of substituents is not particularly limited and can be, for example, 1 to 3.

$R^{1a}$ and $R^{1b}$ in formula (4) are optionally bound to each other to form a ring. Examples of the ring thus formed include the alicyclic rings (cycloalkyl groups), aromatic hydrocarbon rings, and heterocyclic rings mentioned above.

When a naphthylsilole of formula (3) obtained by the production method of the present invention is used as a starting material for GNR, it is preferable that $R^{1a}$ and $R^{1b}$ in formula (4) are both a hydrogen atom, or one is a hydrogen atom and the other is an alkyl group or a (poly) ether group, or $R^{1a}$ and $R^{1b}$ are bound to each other to form a ring.

X in formula (4) is a bromine atom or an iodine atom. From the viewpoint of ease of production of the compound represented by formula (4), X is preferably a bromine atom.

Examples of the optionally branched $C_1$-$C_4$ alkyl group represented by $R^4$ in formula (4) include methyl, ethyl, n-propyl, iso-propyl, n-butyl, iso-butyl, sec-butyl, and tert-butyl groups. The optionally branched $C_1$-$C_4$ halogenated alkyl group is a group in which at least one hydrogen atom of the alkyl group is replaced by a halogen atom, and specific examples include $-CH_2F$, $-CHF_2$, $-CF_3$, $-CH_2Cl$, $-CHCl_2$, and $-CCl_3$.

The aromatic hydrocarbon group represented by $R^4$ in formula (4) can be selected, for example, from aromatic hydrocarbon groups mentioned above. Specific examples include compounds obtained by replacing at least one of the hydrogen atoms on the aromatic hydrocarbon ring of the aromatic hydrocarbon group with at least one substituent. Examples of substituents include optionally branched $C_1$-$C_4$ alkyl groups and a nitro group.

The compound represented by formula (4) is produced by reacting the hydroxyl group of the corresponding brominated (or iodinated) naphthol with sulfonic acid anhydride or sulfonic acid halide, which are commonly used as sulfonyl-protecting groups, as is described below. Therefore, $R^4$ in formula (4) is preferably a substituent derived from sulfonic acid, which is commonly used as a sulfonyl-protecting group. Specific examples include $-CF_3$, $-CH_3$, $-C_6H_4CH_3$ (a tolyl group), and $C_6H_4NO_2$ (a nitrophenyl group).

The compound of formula (4) can be produced, for example, by brominating (or iodinating) a naphthol having the corresponding substituents $R^{1a}$ and $R^{1b}$ by a usual method to obtain a brominated (or iodinated) naphthol, and reacting the brominated (or iodinated) naphthol with the corresponding sulfonylating agent, such as sulfonic acid anhydride or sulfonic acid chloride. Specifically, the compound can be produced by the method described in the Examples below.

In formula (5), examples of the aromatic hydrocarbon group or heterocyclic group represented by $R^2$ include those mentioned above. The type and number of substituents can also be the same as those mentioned above. From the viewpoint of ease of production of formula (5), $R^2$ is preferably an aromatic hydrocarbon group or a heterocyclic group that each has no substituents or that has a $C_1$-$C_{12}$ aromatic hydrocarbon group (e.g., methyl, ethyl, n-propyl, or n-butyl) as a substituent.

Examples of the optionally branched alkyl group represented by $R^{3a}$ and $R^{3b}$ in formula (2) include methyl, ethyl, n-propyl, isopropyl, n-butyl, sec-butyl, tert-butyl, and like groups.

From the viewpoint of ease of production of the compound, $R^{3a}$ and $R^{3b}$ in formula (2) are preferably a methyl group, an ethyl group, or a phenyl group; and it is preferable that $R^{3a}$ and $R^{3b}$ are the same substituent.

X, $R^{1a}$, $R^{1b}$, and $R^2$ in formula (1) can be the same as defined above. When at least one substituent is present, the type and number of substituents can also be the same as those mentioned above. Preferred embodiments are also the same as above. Therefore, specific examples of the compounds of formula (1) include the compounds of the following formulas (1a1) to (1e1):

(1a1)

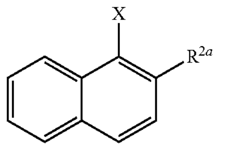

(1b1)

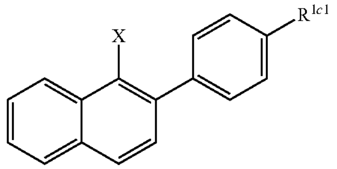

(1c1)

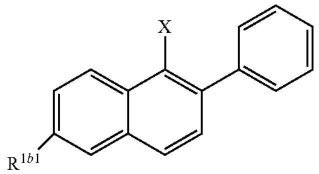

(1d1)

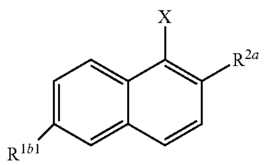

-continued (1e1)

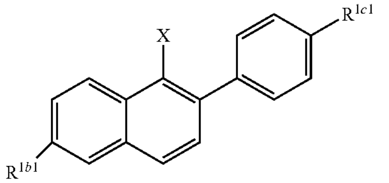

(wherein X is as defined above; $R^{1b1}$ represents a linear or branched $C_1$-$C_{20}$ (preferably $C_1$-$C_{15}$, more preferably $C_1$-$C_{13}$) alkyl group; $R^{1c1}$ represents a $C_1$-$C_{20}$ (preferably $C_2$-$C_{15}$, more preferably $C_2$-$C_{12}$) linear or branched alkyl group; and $R^{2a}$ represents a heterocyclic group). From the viewpoint of the availability of the starting materials, the compounds of formulas (1b1), (1c1), and (1e1), which do not have a heterocyclic group, are preferred. Examples of the linear or branched alkyl groups are the same as those mentioned above. The type and number of substituents are also the same as those mentioned above.

In formula (3), $R^{1a}$, $R^{1b}$, $R^{3a}$, and $R^{3b}$ can be the same as those mentioned above. When at least one substituent is present, the type and number of substituents can also be the same as those mentioned above. Preferred embodiments are also the same as above. The aromatic hydrocarbon ring and heterocyclic ring represented by $R^{2'}$ in formula (3) refer to rings corresponding to rings of the aromatic hydrocarbon group and heterocyclic group represented by $R^2$ in formulas (1) and (5). Examples of the aromatic hydrocarbon ring and heterocyclic ring represented by $R^{2'}$ in formula (3) include those mentioned in the description of $R^2$. When at least one substituent is present, the type and number of substituents can also be the same as those described above. Preferred embodiments are also the same as above. Since step 2 presumably proceeds as shown below, the substituent $R^{2'}$ in formula (3) has a structure such that a silole ring is partially formed by a bond that connects the substituent $R^2$ and a naphthyl group in formula (1) and a bond that connects a carbon atom to which the bond connecting the substituent $R^2$ and the naphthyl group is bonded and a carbon atom adjacent to the carbon atom.

Presumed reaction schemes and examples of compounds produced are described below.

Example in which $R^2$ is a Monovalent Aromatic Hydrocarbon Group (a Benzene Ring) and $nBu_2LaCl$·4LiCl is Used as a Lanthanide- and Lithium-Containing Ate Complex

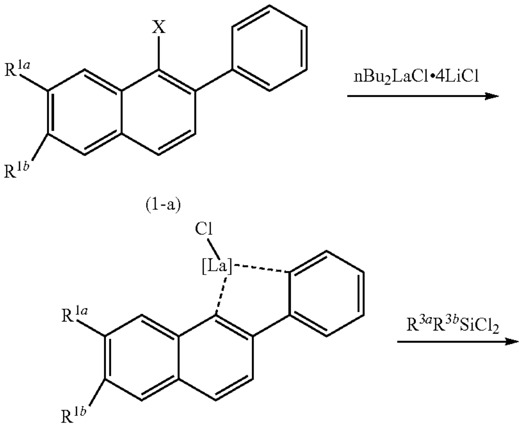

(1-a)

(1-a')

-continued

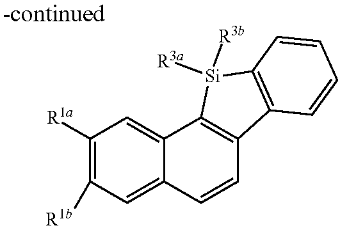

(3-a)

wherein X, $R^{1a}$, $R^{1b}$, $R^{3a}$, and $R^{3b}$ are as defined above; and nBu represents a n-butyl group. The compound represented by formula (1-a') has a model structure of a lanthanide complex of the compound represented by formula (1).

Example in which $R^2$ is a Monovalent Heterocyclic Group (a Thiophene Ring) and $nBu_2LaCl$-4LiCl is Used as a Lanthanide- and Lithium-Containing Ate Complex

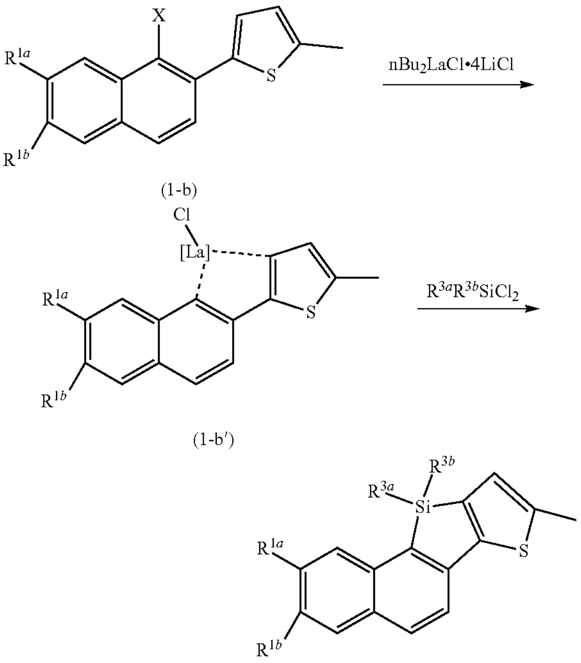

(1-b)

(1-b')

(3-b)

wherein X, $R^{1a}$, $R^{1b}$, $R^{3a}$, and $R^{3b}$ are as defined above; and nBu represents a n-butyl group. Formula (1-b') shows a model structure of a lanthanide complex of the compound represented by formula (1).

(1-1-2) Step 1

In step (1), the compound represented by formula (5) is usually used in an amount of 0.8 to 2.0 moles, and preferably 1.0 to 1.7 moles, per mole of the compound represented by formula (4).

In step (1), a Pd compound, a ligand, and a halogen salt of lithium may be used together. Examples of Pd compounds that can be used together include Pd compounds that are commonly used in cross-coupling reactions. Specific examples include tris(dibenzylideneacetone) dipalladium ($Pd_2$ $(dba)_3$), palladium acetate ($Pd(OAc)_2$), tetrakis(triphenylphosphine) palladium ($Pd(PPh_3)_4$), and the like. Such Pd compounds can be used singly or in a combination of two or more. The amount of Pd compound used is usually 0.1 to 10 mol %, and preferably 1 to 5 mol %, per mole of the compound represented by formula (4).

The ligand that can be used in step (1) is, for example, a phosphine ligand that can be commonly used in cross-coupling reactions. Specific examples include 1,1-bis(diphenylphosphino)methane (DPPM), 1,2-bis(diphenylphosphino)ethane (DPPE), 1,3-bis(diphenylphosphino)propane (DPPP), 1,2-bis(diphenylphosphino)butane (DPPB), 1,1'-bis(diphenylphosphino)ferrocene (DPPF), 2,2'-bis(diphenylphosphino)-1,1'-binaphthyl (BINAP), 4,5'-bis(diphenylphosphino)-9,9'-dimethylxanthene (Xantophos), triphenylphosphine ($PPh_3$) tricyclohexylphosphine ($PCy_3$), and tri-tert-butylphosphine ($P^tBu_3$). These ligands can be used singly or in a combination of two or more. The amount of ligand used is usually 0.1 to 10 mol %, and preferably 1 to 5 mol %, per mole of the compound represented by formula (4).

Specific examples of the halogen salt of lithium in step (1) include LiBr, LiI, and the like. Such lithium halogen salts can be used singly or in a combination of two or more. The amount of lithium halogen salt used is usually 0.7 to 3 moles, and preferably 0.9 to 2 moles, per mole of the compound represented by formula (4).

Step (1) may be performed in the presence of a solvent, if necessary. Examples of usable solvents include ethers. Specific examples of ethers include diethyl ether, cyclopentyl methyl ether, and tetrahydrofuran. The solvent is usually used in an amount of 0.2 to 10 parts by mass, and preferably 0.5 to 5 parts by mass, per part by mass of the compound represented by formula (4).

Step (1) is performed, for example, in the following manner. The compound represented by formula (4) is placed in a reaction vessel optionally together with a Pd compound, a ligand, a halogen salt of lithium, and a solvent, and then cooled to a temperature of −20 to 0° C. After the compound of formula (5) is added at the same temperature, the temperature is raised to 10 to 40° C., and the reaction is allowed to proceed at the same temperature until the reaction is complete.

After completion of the reaction, for example, an acid is added to the reaction mixture to quench the reaction, and an organic solvent and water are then added to the reaction mixture. Liquid separation is performed and the resulting aqueous layer is removed to thereby remove inorganic salts, etc. in the aqueous layer. The organic layer containing the compound is concentrated to thereby obtain a compound represented by formula (1). The obtained compound represented by formula (1) may be purified, for example, by distillation, crystallization, or column chromatography using silica gel, as required.

(1-1-3) Step 2

The lanthanide- and lithium-containing ate complex used in step (2) refers to a complex containing lanthanide and lithium within the complex. Lanthanides are atoms with atomic numbers of 57 to 71, and specific examples include lanthanum, cerium, neodymium, and the like.

Specific examples of the lanthanide- and lithium-containing ate complex include a complex represented by $$R^{20a}{}_{p}MX^{20a}{}_{q}\cdot 4LiX^{20b} \quad (11)$$

(wherein $R^{20a}$ represents an optionally branched $C_1$-$C_4$ alkyl group; M represents a lanthanide atom; and $X^{20a}$ and $X^{20b}$ are the same or different and represent a halogen atom; and p and q are the same or different and represent an integer of 0 to 3 (wherein p+q=3).

Specific examples of optionally branched $C_1$-$C_4$ alkyl groups represented by $R^{20a}$ in formula (11) include methyl, ethyl, n-propyl, iso-propyl, n-butyl, iso-butyl, tert-butyl, and the like. Examples of lanthanide atoms represented by M include atoms with atomic numbers of 57 to 71. Specific examples include lanthanum, cerium, neodymium, and like atoms. Specific examples of halogen atom represented by $X^{20a}$ and $X^{20b}$ include fluorine, chlorine, bromine, and iodine atoms.

Specific examples of the lanthanide- and lithium-containing ate complex having the characteristics mentioned above include $nBu_2LaCl\cdot 4LiCl$, $nBu_2CeCl\cdot 4LiCl$, and $nBu_2NdMe\cdot 4LiCl$.

The lanthanide- and lithium-containing ate complex used in step (2) can be produced, for example, by the method described in the Examples section below.

Lanthanide- and lithium-containing ate complexes can be used singly or in a combination of two or more. Double salts thereof are usually used in an amount of 0.8 to 3 moles, preferably 0.9 to 2 moles, per mole of the compound represented by formula (1).

The step (2) may be performed in the presence of a solvent, if necessary. Examples of usable solvents include ethers. Specific examples of ethers include diethyl ether, cyclopentyl methyl ether, and tetrahydrofuran. Solvents can be used singly or in a combination of two or more. The amount of solvent used is usually 0.5 to 20 times by weight, and preferably 1 to 10 times by weight, relative to the weight of the compound represented by formula (1).

The step (2) is performed, for example, in the following manner. After the compound represented by formula (1) and the solvent are placed in a reaction vessel and the temperature is adjusted to −20° C. or less, preferably −75 to −30° C., a lanthanide and lithium-containing ate complex is added at the same temperature and the resulting mixture is stirred for a certain period of time to thereby produce the lanthanide complex of formula (1). Subsequently, after the temperature is increased to −10° C. to 10° C., the silyl compound represented by formula (2) is placed in the reaction vessel at the same temperature to allow the lanthanide complex of formula (1) to react with the silyl compound represented by formula (2). From the viewpoint of increasing the reaction rate, the temperature of the reaction mixture may be raised to 10 to 40° C., as necessary, after adding the silyl compound represented by formula (2).

After completion of the reaction, for example, an organic solvent and water are added to the reaction mixture, liquid separation is performed, and the resulting aqueous layer is removed to thereby remove inorganic salts etc. in the aqueous layer. The organic layer containing the compound is concentrated to thereby obtain a compound represented by formula (1). The obtained compound represented by formula (1) may be purified, for example, by distillation, crystallization, or column chromatography using silica gel, as required.

(1-2) Naphthylsilole Having a Heteroaromatic Ring

According to the method for producing a naphthylsilole of the present invention, a naphthylsilole with a heteroaromatic ring that has a structure represented by formula (3a):

(3a)

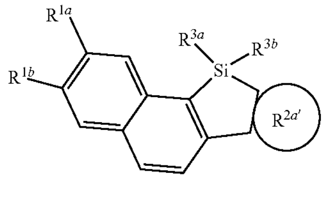

(wherein $R^{1a}$, $R^{1b}$, $R^{2a'}$, $R^{3a}$, and $R^{3b}$ are as defined above) can be produced. In formula (3a), examples of $R^{1a}$, $R^{1b}$, $R^{3a}$, and $R^{3b}$ include those mentioned above. The heteroaromatic ring represented by $R^{2a'}$ and the structure thereof are also the same as those mentioned above. When at least one substituent is present, the type and number of substituents are also the same as those mentioned above. Preferable examples of the heteroaromatic ring represented by $R^{2a'}$ include furan, thiophene, pyrrole, pyridine, and the like.

Specific examples of the naphthylsilole with a heteroaromatic ring that has a structure represented by formula (3a) include naphthylsiloles represented by formulas (3a1), (3a2), and (3a3):

(3a1)

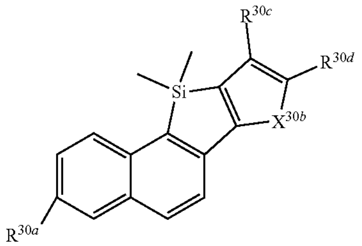

(3a2)

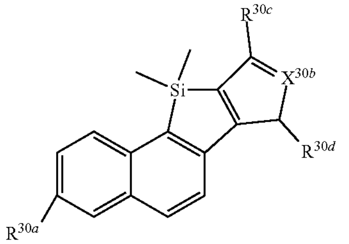

(3a3)

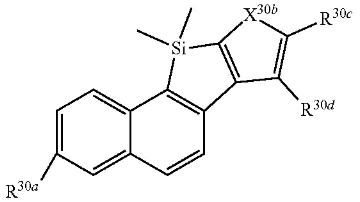

(wherein $R^{30a}$ represents a hydrogen atom or an alkyl group; $R^{30c}$ and $R^{30d}$ are the same or different and represent a hydrogen atom, an alkyl group, or an aromatic hydrocarbon group; when $R^{30c}$ and $R^{30d}$ are adjacent to each other, $R^{30c}$ and $R^{30d}$ are optionally bound to each other to form a ring; $X^{30b}$ represents an oxygen atom, a sulfur atom, or $NR^{30e}$ (wherein $R^{30e}$ represents an alkyl group, an aromatic hydrocarbon group, an acetyl group, a tert-butoxycarbonyl group, a methylsulfonyl group, or a tosyl group); and naphthylsiloles represented by formulas (3a4), (3a5), (3a6), and (3a7):

(3a4)

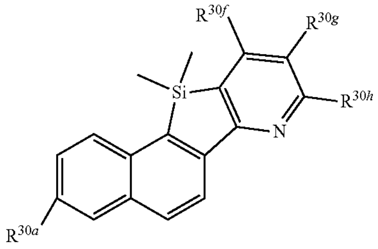

-continued (3a5)

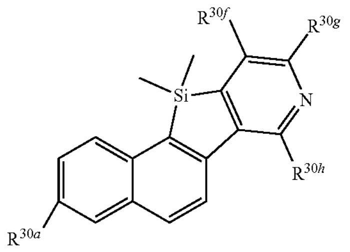

(3a6)

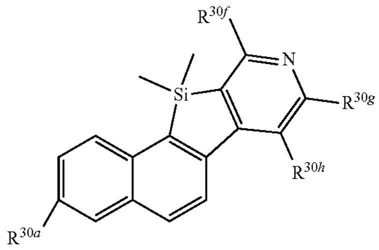

(3a7)

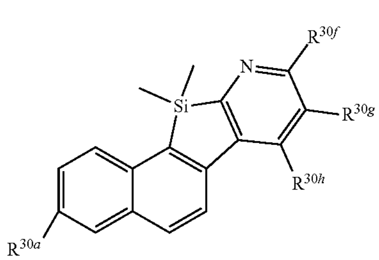

(wherein $R^{30a}$ represents a hydrogen atom or an alkyl group; $R^{30f}$, $R^{30g}$ and $R^{30h}$ are the same or different and represent a hydrogen atom, an alkyl group, or an aromatic hydrocarbon group; when $R^{30f}$, $R^{30g}$ and $R^{30h}$ are adjacent, $R^{30e}$, $R^{30f}$, and $R^{30g}$ are optionally bound to each other to form a ring). Specific examples include naphthylsiloles represented by the following formulas:

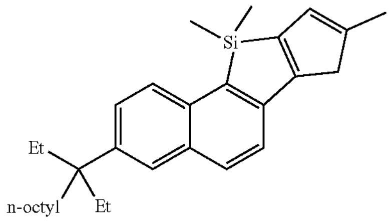

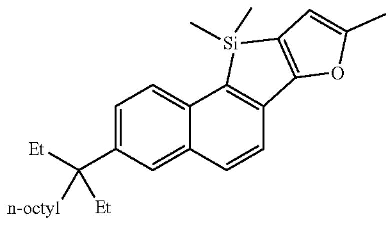

-continued

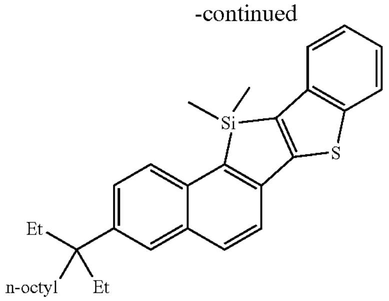

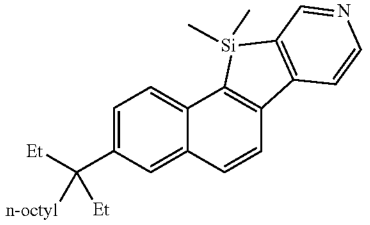

(wherein n-octyl represents an n-octyl group and Et represents an ethyl group).

In the above, examples of the alkyl group represented by $R^{30a}$, $R^{30c}$, $R^{30d}$, $R^{30e}$, $R^{30f}$, $R^{30g}$ and $R^{30h}$, aromatic hydrocarbon groups represented by $R^{30c}$, $R^{30d}$, $R^{30e}$, $R^{30f}$, $R^{30g}$, and $R^{30h}$, a ring formed when $R^{30c}$ and $R^{30d}$ are bound to each other, and a ring formed when $R^{30e}$, $R^{30f}$, and $R^{30g}$ are bound to each other can be the same as those mentioned above. When at least one substituent is present, the type and number of substituents can also be the same as those mentioned above. Preferred embodiments are also the same as above.

(1-3) GNR Having a Heteroaromatic Ring

The GNR of the present invention has at least one structural unit represented by formula (6):

(6)

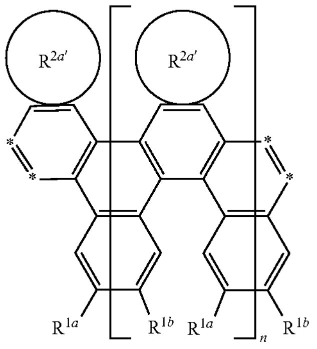

(wherein * represents a bonding point; n represents an integer of 0 or more; $R^{1a}$, $R^{1b}$, and $R^{2a'}$ are as defined above; and $R^{1a}$ and $R^{1b}$ bound to the same benzene ring are optionally bound to each other to form a ring). In formula (6), $R^{1a}$, $R^{1b}$, and $R^{2a'}$ can be the same as those mentioned above. When at least one substituent is present, the type and number of substituents can also be the same as those mentioned above. Preferred embodiments are also the same as above. However, when $R^{1a}$ and $R^{1b}$ are bound to each other to form a ring, $R^{1a}$ and $R^{1b}$ bound to the same benzene ring are bound to each other to form a ring.

The GNR of the present invention is produced, for example, by the method of PTL 1 mentioned above. Accordingly, at least one end may have a structural unit represented by formula (7):

(7)

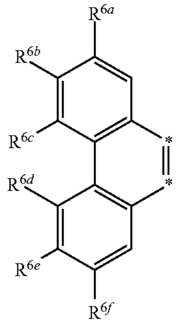

(wherein the dotted line represents no bond or a single bond; * represents a bonding point; $R^{6a}$, $R^{6b}$, $R^{6c}$, $R^{6d}$, $R^{6e}$, and $R^{6f}$ are the same or different and represent a hydrogen atom, a halogen atom, an alkyl group, a cycloalkyl group, a (poly) ether group, an ester group, a boronic acid group or an ester group of boronic acid, a monovalent aromatic hydrocarbon group, or a monovalent heterocyclic group; and $R^{6c}$ and $R^{6d}$ are optionally bound to each other to form a ring).

Examples of the halogen atom represented by $R^{6a}$, $R^{6b}$, $R^{6c}$, $R^{6d}$, $R^{6e}$, and $R^{6f}$ in formula (7) include fluorine, chlorine, bromine, and iodine atoms.

In formula (7), examples of the alkyl group represented by $R^{6a}$, $R^{6b}$, $R^{6c}$, $R^{6d}$, $R^{6e}$, and $R^{6f}$ can be the same as those mentioned above. When at least one substituent is present, the type and number of substituents can also be the same as those mentioned above. Preferred embodiments are also the same as above.

In formula (7), examples of the cycloalkyl group represented by $R^{6a}$, $R^{6b}$, $R^{6c}$, $R^{6d}$, $R^{6e}$ and $R^{6f}$ can be the same as those mentioned above. When at least one substituent is present, the type and number of substituents can also be the same as those mentioned above. Preferred embodiments are also the same as above.

The (poly)ether group represented by $R^{6a}$, $R^{6b}$, $R^{6c}$, $R^{6d}$, $R^{6e}$, and $R^{6f}$ in formula (7) refers to an ether group or a polyether group. Examples of the (poly)ether group can be the same as those mentioned above. When at least one substituent is present, the type and number of substituents can also be the same as those mentioned above. Preferred embodiments are also the same as above.

In formula (7), examples of the ester group represented by $R^{6a}$, $R^{6b}$, $R^{6c}$, $R^{6d}$, $R^{6e}$, and $R^{6f}$ can be the same as those mentioned above. When at least one substituent is present, the type and number of substituents can also be the same as those mentioned above. Preferred embodiments are also the same as above.

Examples of the boronic acid group or ester group of boronic acid represented by $R^{6a}$, $R^{6b}$, $R^{6c}$, $R^{6d}$, $R^{6e}$, and $R^{6f}$ in formula (7) include boryl, pinacolatoboryl, and the like.

In formula (7), examples of aromatic hydrocarbon or heterocyclic groups represented by $R^{6a}$, $R^{6b}$, $R^{6c}$, $R^{6d}$, $R^{6e}$ and $R^{6f}$ can be the same as those mentioned above. The type and number of substituents can also be the same as those mentioned above.

From the viewpoint of the availability of starting materials and water solubility, preferable examples of $R^{6a}$, $R^{6b}$, $R^{6c}$, $R^{6d}$, $R^{6e}$, and $R^{6f}$ in formula (7) are a hydrogen atom, alkyl groups, (poly)ether groups, and the like. More preferable examples of alkyl groups are branched alkyl groups, even more preferably isopropyl, isobutyl, sec-butyl, tert-butyl, isopentyl, neopentyl, isohexyl, 1,1-dimethylbutyl, 2,2-dimethylbutyl, and 3,3-dimethylbutyl, and particularly preferably tert-butyl.

In formula (7), $R^{6c}$ and $R^{6d}$ can be bound to each other to form a ring. Examples of the ring thus formed include the aromatic hydrocarbon rings and heterocyclic rings mentioned above.

Since the GNR of the present invention comprises at least one structural unit represented by formula (6) and at least one structural unit represented by formula (7) as stated above, the GNR of the present invention preferably has a structural unit represented by formula (8):

(8)

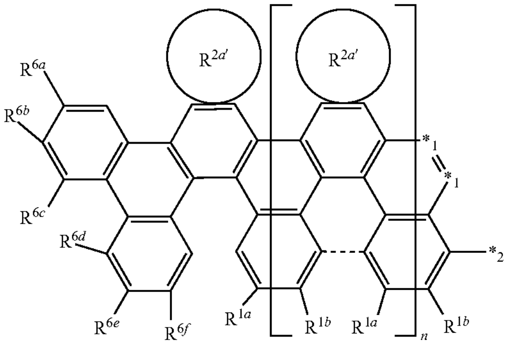

(wherein the dotted lines are the same and different and represent no bond or a single bond; and *1 represents a bonding point; *2 represents a bonding point when the dotted line connecting to *2 is a single bond; n represents an integer of 0 or more; $R^{1a}$, $R^{1b}$, $R^{2a'}$, $R^{6a}$, $R^{6b}$, $R^{6c}$, $R^{6d}$, $R^{6e}$, and $R^{6f}$ are as defined above; $R^{1a}$ and $R^{1b}$ bound to the same benzene ring may be bound to each other to form a ring; and $R^{6c}$ and $R^{6d}$ may be bound to each other to form a ring). In formula (8), examples of $R^{1a}$, $R^{1b}$, $R^{2a'}$, $R^{6a}$, $R^{6b}$, $R^{6c}$, $R^{6d}$, $R^{6e}$, and $R^{6f}$ can be the same as those mentioned above. When the compound has at least one substituent, the type and number of substituents can also be the same as those mentioned above. Preferred embodiments are also the same as above.

Examples of the structural unit represented by formula (8) include structural units represented by the following formulas (8a1), (8a2), (8a3), (8a4), (8a5), (8a6), (8a7), (8a8), (8a9), (8a10), (8a11), (8a12), (8a13), and (8a14):

(8a1)

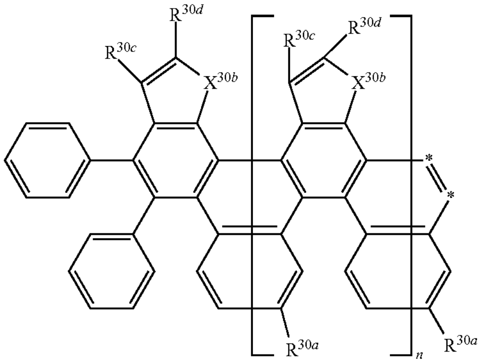

-continued (8a2)

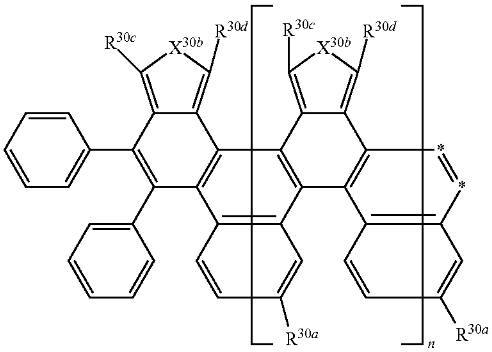

(8a3)

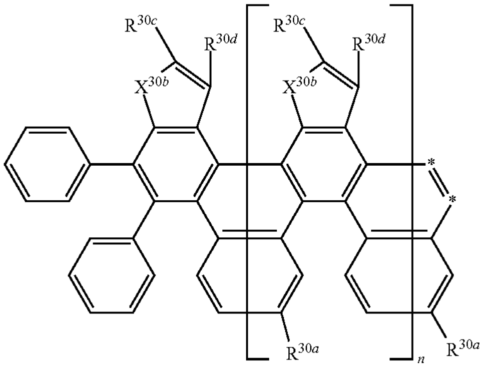

(8a4)

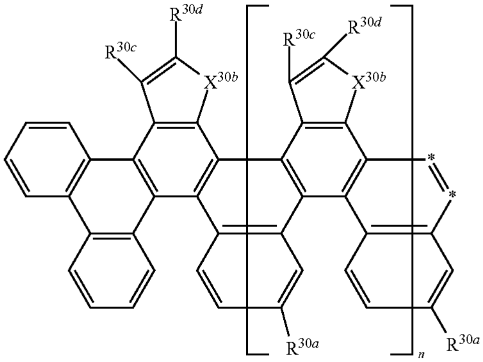

(8a5)

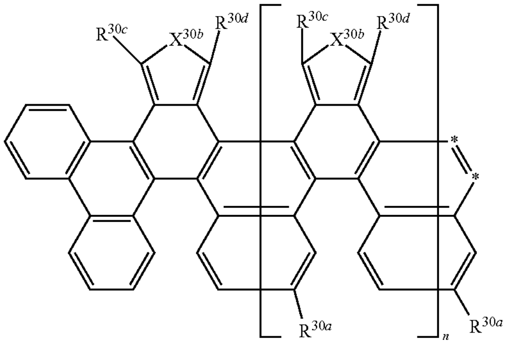

-continued
(8a6)
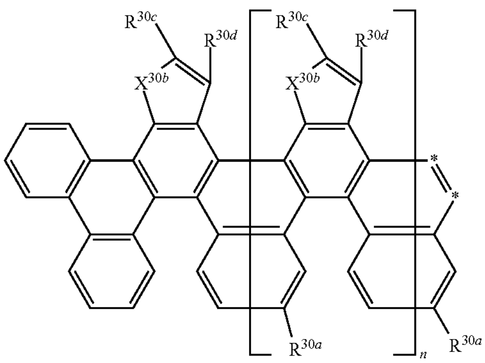
(8a7)
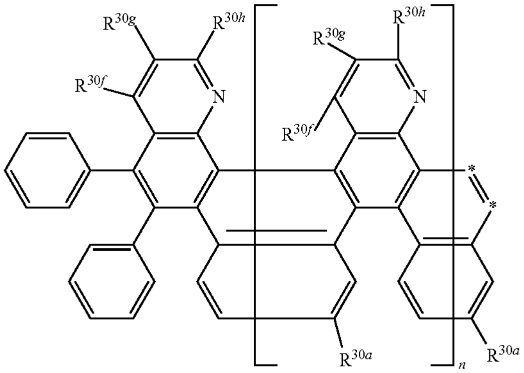
(8a8)
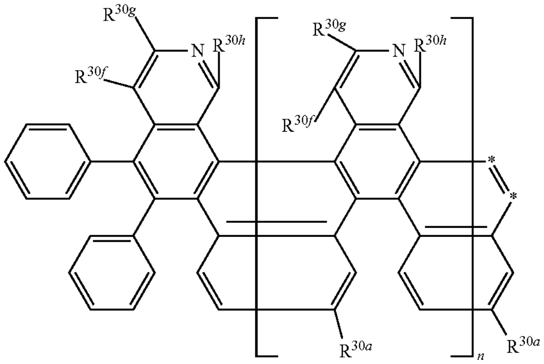
(8a10)
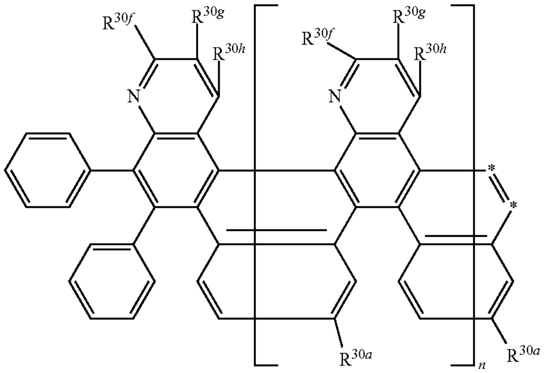
-continued
(8a11)
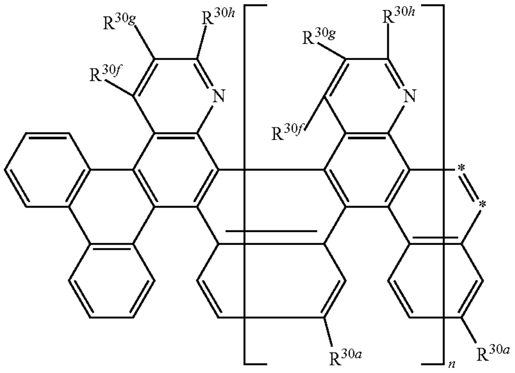
(8a12)
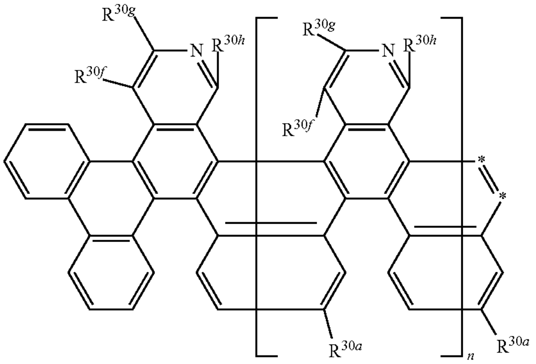
(8a13)
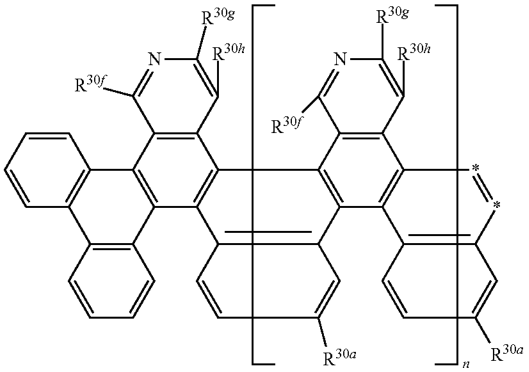
(8a14)
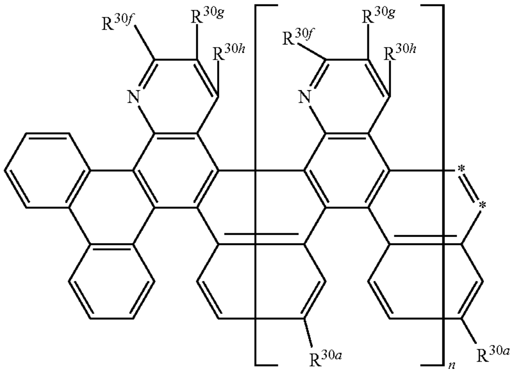
(wherein * represents a bonding point; n represents an integer of 0 or more; $R^{30a}$, $R^{30c}$, $R^{30d}$, $X^{30b}$, $R^{30f}$, $R^{30g}$, and $R^{30h}$ are as defined above). Specific examples include structural units represented by the following formula:
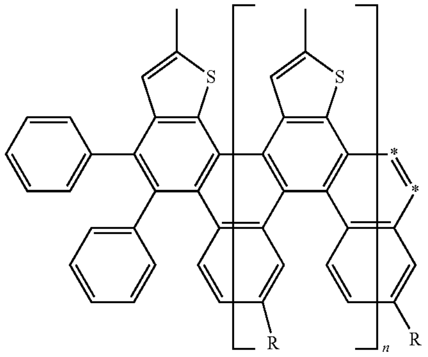
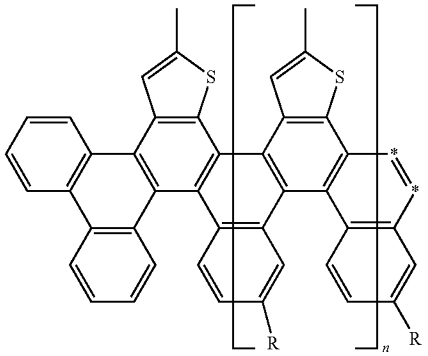
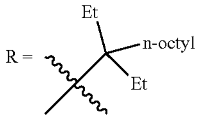
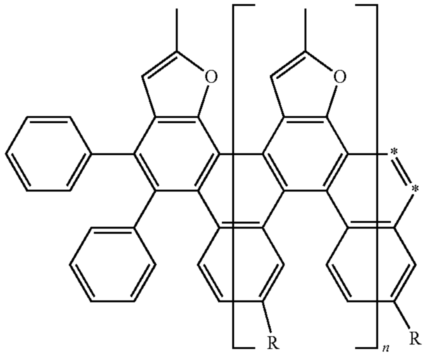
-continued
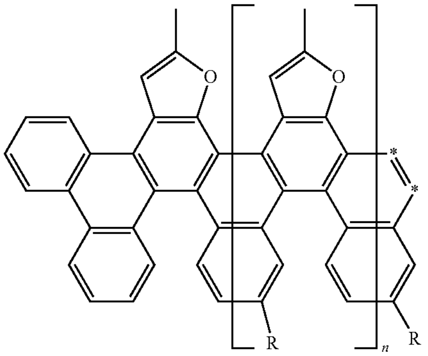
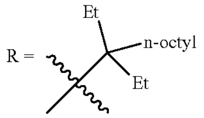
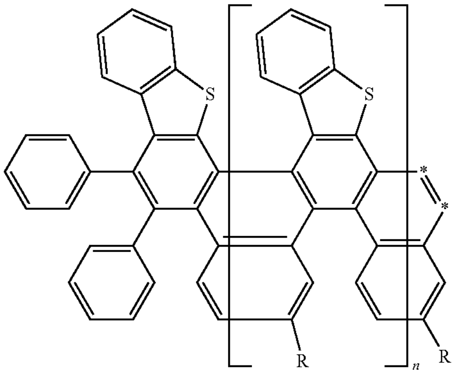
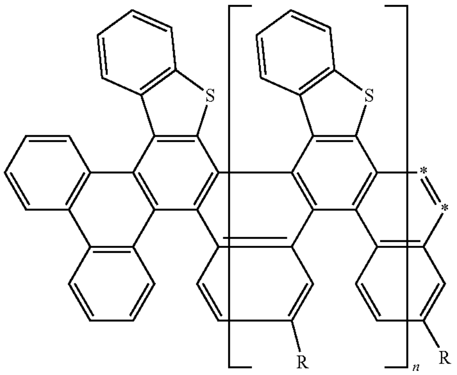
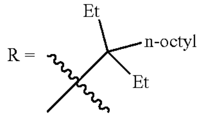
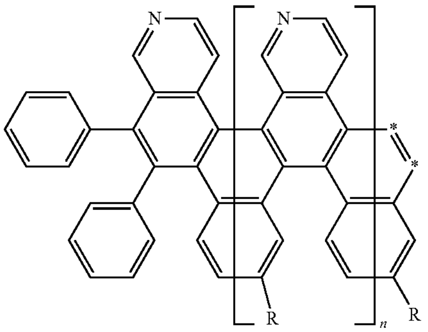

-continued

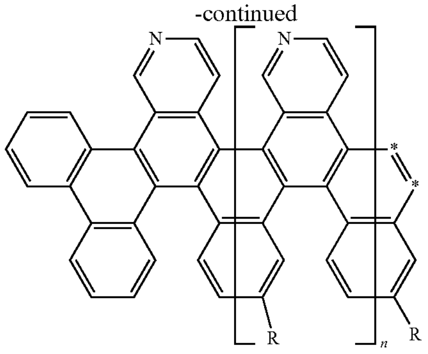

R = 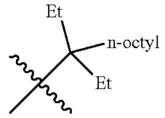

(wherein * represents a bonding point; n represents an integer of 0 or more; n-octyl represents a n-octyl group; and Et represents an ethyl group).

Further, GNRs having the following structural units can also be formed by subjecting GNRs having the structural units described above to a ring fusion reaction. The ring fusion reaction can be performed, for example, by the method described in PTL 1 mentioned above (specifically, for example, the Scholl reaction (dehydrogenative cyclization reaction)).

Specific examples of the GNRs having been subjected to a ring fusion reaction include GNRs having structural units represented by the following formulas (9a1), (9a2), (9a3), (9a4), (9a5), (9a6), and (9a7):

(9a1)

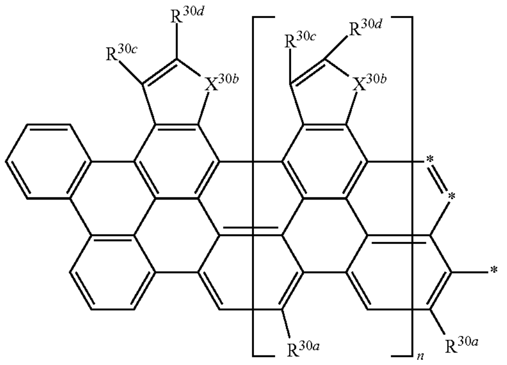

(9a2)

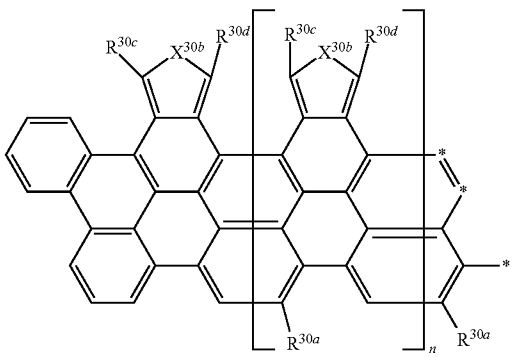

-continued (9a3)

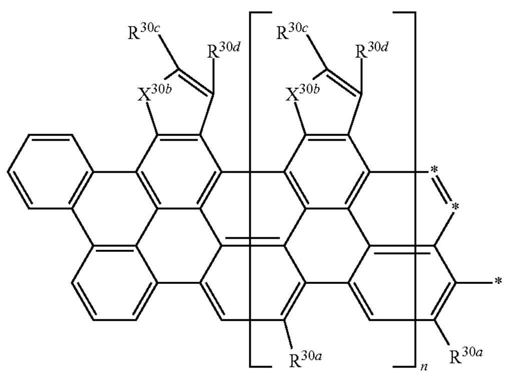

(9a4)

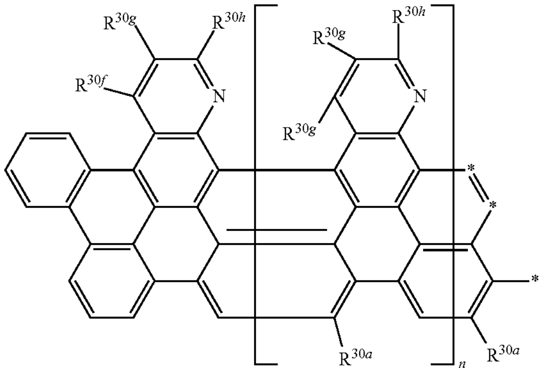

(9a5)

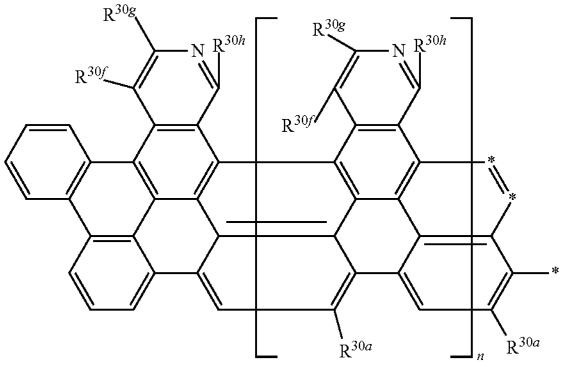

(9a6)

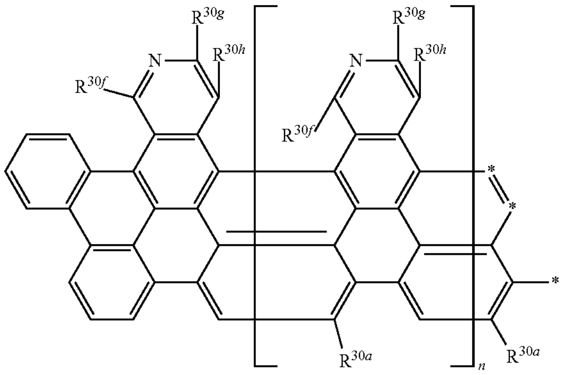

-continued (9a7)

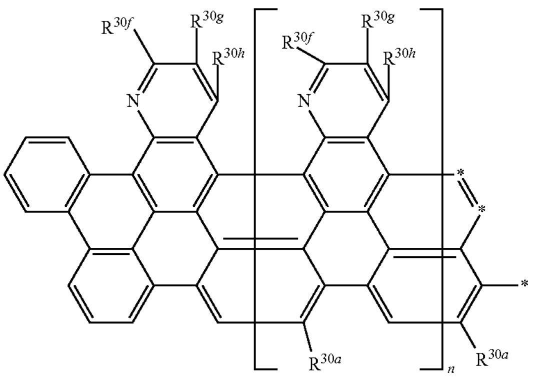

(wherein * represents a bonding point; n represents an integer of 0 or more; $R^{30a}$, $R^{30c}$, $R^{30d}$, $X^{30b}$, $R^{30f}$, $R^{30g}$, and $R^{30h}$ are as defined above; and when $R^{30h}$ and $R^{30f}$ in formulas (9a5) and (9a6) are each an hydrogen atom, a single bond is formed); and more specifically structural units represented by the following formulas:

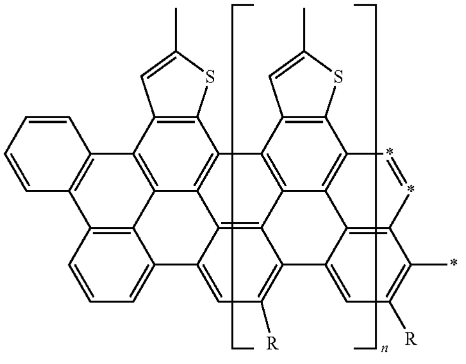

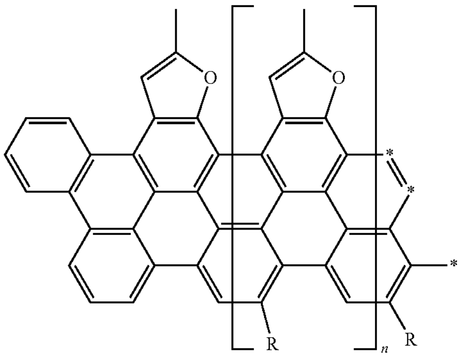

R=

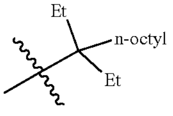

-continued

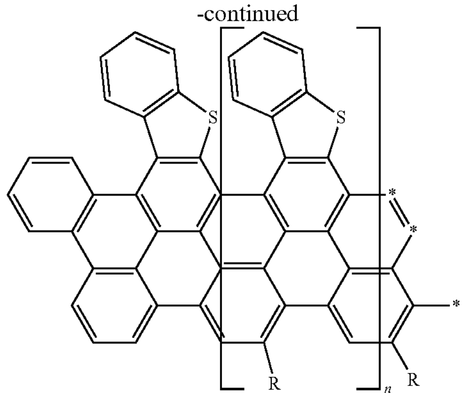

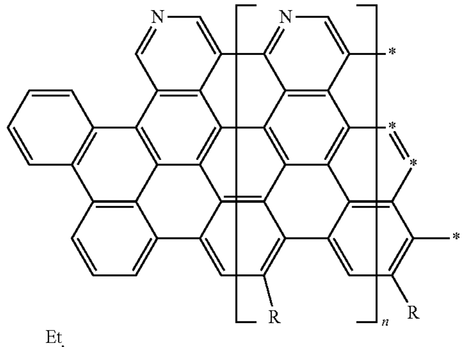

R=

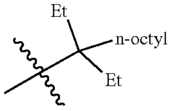

wherein * represents a bonding point; n represents an integer of 0 or more; n-octyl represents a n-octyl group; and Ft represents an ethyl group.

In the GNR of the present invention, n in formulas (6) and (8) is not particularly limited and is an integer of 0 or more, and can be appropriately selected according to the required characteristics. For example, n is preferably 10 to 1000, and more preferably 10 to 500. It is also possible to form oligomers of formulas (6) and (8) wherein n is 1 to 99, preferably 2 to 49, more preferably 2 to 19, and even more preferably 3 to 9. The n in the GNR of the present invention is calculated from the number average molecular weight measured in terms of polystyrene by gel permeation chromatography.

The number average molecular weight of the GNR of the present invention is not particularly limited and can be selected according to the required characteristics. From the viewpoint of solubility etc., the number average molecular weight is, for example, preferably 10000 or more, more preferably 15000 to 300000, even more preferably 20000 to 200000, and particularly preferably 30000 to 150000. For example, when an oligomer is to be formed, the GNR of the present invention can have a number average molecular weight of, for example, 500 to 5000. The number average molecular weight of the GNR of the present invention is determined by gel permeation chromatography in terms of polystyrene.

The length of the GNR of the present invention is preferably 10 nm or longer, more preferably 20 to 500 nm, even more preferably 50 to 400 nm, and particularly preferably 100 to 300 nm. For example, when the GNR of the present invention is formed as an oligomer, the length of the GNR of the present invention can be appropriately selected according to the required characteristics. GNRs having a longer length are expected to be applied to semiconductors, solar cells, etc., while GNRs having a shorter length are expected to be applied to organic EL devices etc.

EXAMPLES

The present invention is described below in more detail with reference to Examples etc. However, the scope of the invention is not limited to these Examples.

(1) NMR Measurement $^{1}$H-NMR and $^{13}$C-NMR were measured using tetramethylsilane as an internal standard and using deuterated chloroform ($CDCl_3$) as a solvent, and recorded by a JEOL-ESC600 ($^{1}$H 600 MHz, $^{13}$C 150 MHz) or JEOL-ESC400 ($^{1}$H 400 MHz, $^{13}$C 100 MHz, $^{19}$F 376 MHz) spectrometer. Each data item obtained was described as follows:

chemical shift, multiplicity (s=singlet, d=doublet, dd=doublet of doublets, ddd=doublet of doublet of doublets, t=triplet, td=triplet of doublets, q=quartet, m=multiplet), coupling constant (Hz), and integration.

(2) Fast Atomic Bombardment Mass Spectrometry (FAB-MS)

For FAB-MS, 3-nitrobenzyl alcohol was used as the matrix, and high-resolution mass spectra (HRMS) were obtained by a double-focusing mass spectrometer (JEOL JMS-700).

(3) Measurement of Molecular Weight (Mn) and Mw/Mn (PDI) of GNR by Size Exclusion Chromatography (SEC)

Analysis was performed using the following device under the following conditions.

Device: Shimadzu Prominence 2000

Column: TOSOH TSKgel Multipore $H_{XL}$-M SEC column 7.8 mm×300 mm×2 columns (connected in series) produced by Tosoh Corporation, measurement temperature: 40° C.

Eluent: tetrahydrofuran containing 0.1 mass % tetra-n-butylanmonium bromide

Standard molecular weight: in terms of standard polystyrene (TOSOH TSKgel polystyrene standard).

(4) Materials Used for Analysis/Purification in the Examples Below Etc.

Thin-layer chromatography for analysis (TLC): E. Merck silica gel 60 F254 pre-coated plate (0.25 mm)

Silica for column chromatogram: KANTO silica gel 60N (spherical, neutral, 40 to 100 μm)

Metal scavenger: Biotage Metal Scavenger Si-TMT.

(5) Preparative Size Exclusion Chromatography (SEC) and Preparative SEC Conditions Instrument: JAI LC-9210II NEXT, produced by Japan Analytical Industry Co., Ltd.

Column: JAIGEL-3H/JAIGEL-5H, produced by Japan Analytical Industry Co., Ltd.

Solvent: chloroform

Flow rate: 3.5 mL/min.

Production Example 1

Production Example of 3-chloro-3-ethylundecane

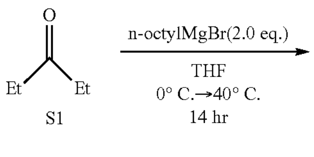

S1

-continued

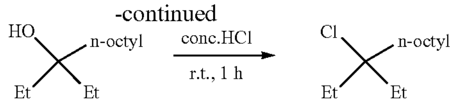

S2 S3 wherein Et represents an ethyl group; n-octyl represents a n-octyl group; and THF represents tetrahydrofuran.

Magnesium turnings (5.8 g, 240 mmol) were placed in a 200-mL two-necked round-bottom flask containing a magnetic stirrer and stirring was started. The flask was heated with a heat gun under reduced pressure for 10 minutes and then purged with nitrogen. After purging with nitrogen, the flask was cooled to room temperature. n-Octyl bromide (37.1 mL, 225 mmol) and THF (100 mL) were added to the flask at the same temperature. Further, after 1,2-dibromoethane (2 drops, for activation of the magnesium turnings) was added, the temperature was raised to 40° C. and the mixture was stirred at the same temperature for 1 hour to prepare the corresponding Grignard reagent. 3-Pentanone (compound S1; 16.0 mL, 150 mmol) and THF (100 mL) were placed in another 300-mL two-necked round-bottom flask containing a magnetic stirrer. The Grignard's reagent solution prepared as described above was added dropwise to the mixture of 3-pentanone and THF with vigorous stirring at 0° C. The temperature was increased to 40° C. and the mixture was stirred at the same temperature for 14 hours.

After the progress of the reaction was confirmed by TLC, the resulting reaction mixture was quenched with water. The organic layer was washed with a saturated aqueous $NH_4Cl$ solution and water and then dried over $Na_2SO_4$. $Na_2SO_4$ was then filtered and the solvent was removed under reduced pressure. A crude product of 3-ethyl-3-hydroxylundecane (compound S2) was thus obtained.

Subsequently, after concentrated hydrochloric acid (35 mL) was added to a 200-mL two-necked round-bottom flask containing the crude product of compound S2 obtained by the above operation and a magnetic stirrer, the mixture was stirred at room temperature for 1 hour. Organic matter was extracted from the obtained mixture with diethyl ether (100 mL) 3 times. The extracted organic layers were combined into one, washed with brine, and then dried over $Na_2SO_4$. $Na_2SO_4$ was then filtered and the solvent was removed under reduced pressure to obtain a crude product. The obtained crude product was purified by flash column chromatography on silica gel (eluent: hexane) to give 3-chloro-3-ethylundecane (compound S3; 17.0 g, 76% yield).

Production Example 2

Production Example of a Naphthol Having a Substituent

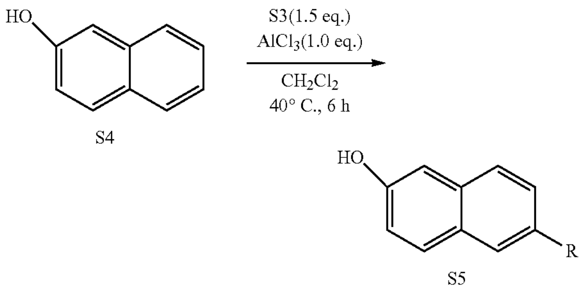

S4

S5

-continued

S3 =
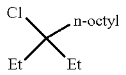

R =
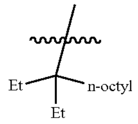

wherein Et represents an ethyl group; and n-octyl represents a n-octyl group.

2-Naphthol (compound S4; 12.0 g, 83.2 mmol), 3-chloro-3-ethylundecane (compound S3; 27.3 g, 124.9 mol), and $CH_2Cl_2$ (120 mL) were placed in a 200-mL two-necked round-bottom flask containing a magnetic stirrer in a nitrogen atmosphere, and stirring was started. $AlCl_3$ (11.0 g, 83.2 mmol) was then added at room temperature. The temperature was then raised to 40° C. After stirring overnight at the same temperature, methanol (30 mL) was added to quench the reaction.

The organic layer was then washed with water and dried over $Na_2SO_4$. $Na_2SO_4$ was filtered and the solvent was removed under reduced pressure to give a crude product. The obtained crude product was purified by open-column chromatography on silica gel (eluent: $CH_2Cl_2$/hexane=4:1) to obtain 6-(3-ethyl-undecyl)-2-naphthol (compound S5) as a colorless oil (13.0 g, 48% yield).

Example 1

Production Example of Compound Represented by Formula (4)

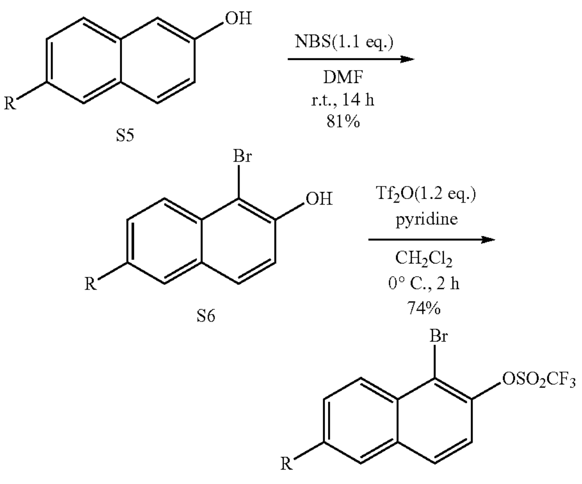

S5
S6
(4-1)

R =
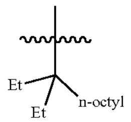

wherein NBS represents N-bromosuccinimide; DMF represents N,N-dimethylformamide; Et represents an ethyl group; and n-octyl represents a n-octyl group.

S5 (17.00 g, 52.1 mmol) and DMF (112 ml) were placed in a 1-L two-necked round-bottom flask containing a magnetic stirrer under a nitrogen atmosphere. After stirring was started, NBS (10.19 g, 57.3 mmol) dissolved in DMF (200 ml) was added slowly dropwise at room temperature for 30 minutes. After stirring at room temperature for 14 hours, the mixture was quenched with water and extracted with ethyl acetate (40 ml) 3 times. The combined organic layers were washed with brine and then dried over $Na_2SO_4$. $Na_2SO_4$ was filtered and the solvent was removed under reduced pressure to obtain a crude product. The crude product was purified by open-column chromatography on silica gel (eluent: hexane/ethyl acetate=20:1) to obtain 1-bromo-6-(3-ethyl-undecyl)-2-naphthol (compound S6) as a colorless oil (17.16 g, yield: 81%).

Compound S6 (17.16 g, 42.3 mmol) and $CH_2Cl_2$ (84 ml) were placed in a 100 ml two-necked round-bottom flask containing a magnetic stirrer under a nitrogen atmosphere, and stirring was started. Then, after cooling to 0° C., pyridine (4.11 ml, 50.8 mmol) was added at the same temperature and further stirred at the same temperature for 10 minutes. Trifluoromethanesulfonic anhydride (7.83 ml, 46.6 mmol) was then added and stirred at 0° C. for 2 hours. Water was then added to quench the reaction. After organic matter was extracted from the resulting reaction mixture with ethyl acetate (30 ml) 3 times, the combined organic layers were washed with brine and then dried over $Na_2SO_4$. $Na_2SO_4$ was then filtered and the solvent was removed under reduced pressure to obtain a crude product. The obtained crude product was purified by open-column chromatography on silica gel (eluent: hexane) to obtain 1-bromo-6-(3-ethyl-3-undecyl)-2-naphthyltrifluoromethanesulfonate (compound 4-1) as a yellow oil (16.9 g, yield: 74%). The analytical values of the obtained compound (4-1) are as follows.

$^1$H NMR (400 MHz, $CDCl_3$): δ 8.23 (d, J=8.7 Hz, 1H), 7.85 (d, J=8.7 Hz, 1H), 7.68-7.73 (m (dd, d), 2H), 7.40 (d, J=8.7 Hz, 1H), 1.78 (q, J=7.3 Hz, 4H), 1.68-1.75 (m, 2H), 1.17-1.31 (m, 10H), 0.85 (t, J=6.9 Hz, 3H), 0.67 (t, J=7.3 Hz, 6H); $^{19}$F NMR (382 MHz, $CDCl_3$): δ-73.2.

Example 2

Production Example (1) of Compound Represented by Formula (1)

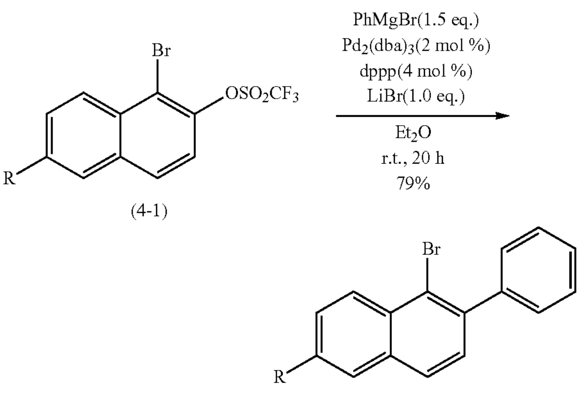

(4-1)
(1-1)

R =
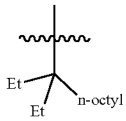

wherein Ph represents a phenyl group; dba represents dibenzylideneacetone; dppp represents 1,3-bis(diphenylphosphino)propane; Et represents an ethyl group; and n-octyl represents a n-octyl group.

Compound (4-1) (7.54 g, 14.0 mmol), $Pd_2(dba)_3$ (231 mg, 0.28 mmol), dppp (231 mg, 0.56 mmol), LiBr (1.22 g, 14.0 mmol), and $Et_2O$ (12 ml) were placed in a 100-ml two-necked round-bottom flask containing a magnetic stirrer under a nitrogen atmosphere, and stirring was started. Then, after cooling to 0° C., phenylmagnesium bromide (3.0M in $Et_2O$, 7.01 ml) was added dropwise with stirring at the same temperature. The temperature was raised to room temperature and the mixture was further stirred at the same temperature for 20 hours, then quenched with 1M HCl and extracted with ethyl acetate (20 ml) 3 times. The combined organic layers were washed with brine and then dried over $Na_2SO_4$. $Na_2SO_4$ was filtered and the solvent was removed under reduced pressure to obtain a crude product. The crude product was purified by open-column chromatography on silica gel (eluent: hexane/ethyl acetate=20:1) to obtain 1-bromo-6-(3-ethyl-undecyl)-2-phenylnaphthalene (compound 1-1) as a pale yellow oil (5.14 g, yield: 79%). The analytical values of the obtained compound (1-1) are as follows.

$^1H$ NMR (400 MHz, $CDCl_3$): δ 8.32 (d, J=9.1 Hz, 1H), 7.81 (d, J=9.1 Hz, 1H), 7.71 (d, J=2.0 Hz, 1H), 7.64 (dd, J=2.0, 9.1 Hz, 1H), 7.45-7.49 (m, 4H), 7.41 (m, 2H), 1.81 (q, J=7.5 Hz, 4H), 1.69-1.76 (m, 2H), 1.16-1.32 (m, 10H), 0.98-1.08 (m, 2H), 0.86 (t, J=7.5 Hz, 3H), 0.68 (t, J=7.5 Hz, 6H).

$^{13}C$ NMR (100 MHz, $CDCl_3$): δ 146.2, 142.4, 139.9, 133.4, 130.6, 129.7 (2C), 128.3, 127.9 (2C), 127.5, 127.4 (2C), 127.2, 125.8, 122.1, 43.7, 36.4, 31.9, 30.5, 29.5, 29.3, 28.9 (2C), 23.5, 22.6, 14.1, 8.1 (2C). HRMS (FAB+) m/z calcd. for $C_{29}H_{37}Br[M+H]^+$; 464.2079, found 464.2073.

Example 3

Production Example (2) of Compound Represented by Formula (1)

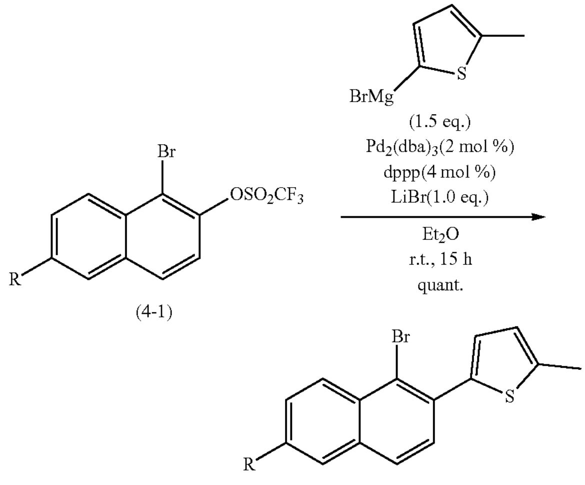

(4-1)

(1-2)

R =

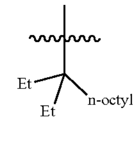

wherein dba represents dibenzylideneacetone; dppp represents 1,3-bis(diphenylphosphino)propane; Et represents an ethyl group; and n-octyl represents a n-octyl group.

Magnesium turnings (90.4 mg, 3.72 mmol) were placed in a Schlenk tube containing a magnetic stirrer, and stirring was started. The Schlenk tube was heated with a heat gun under reduced pressure and then purged with nitrogen. After purging with nitrogen, the tube was cooled to room temperature, and diethyl ether (1 ml) was added to the Schlenk tube at the same temperature. Further, 2-bromo-5-methylthiophene (0.139 ml, 2.79 mmol) was added dropwise at room temperature, and stirring was performed at the same temperature for 1 hour to prepare a Grignard reagent of 2-bromo-5-methylthiophene.

After compound (4-1) (1.00 g, 1.86 mmol), LiBr (0.162 mg, 1.86 mmol), dppp (30.7 mg, 74.4 μmol), $Pd_2(dba)_3$ (34.0 mg, 37.2 μmol), and $Et_2O$ (1 ml) were placed in another test tube with a lid, stirring was started. After cooling to 0° C., the Grignard reagent of 2-bromo-5-methylthiophene prepared separately was added dropwise using a syringe at 0° C. After the dropwise addition, the temperature was raised to room temperature and stirring was performed at the same temperature for 15 hours.

After completion of the reaction, the obtained reaction mixture was quenched with 1M hydrochloric acid. After liquid separation was performed to separate an oil layer and an aqueous layer, ethyl acetate was added to the separated aqueous layer, and organic matter was extracted from the aqueous layer. The separated oil layer and the organic layer obtained by extracting organic matter from the aqueous layer were combined and dried over $Na_2SO_4$. $Na_2SO_4$ was then filtered and the solvent was removed under reduced pressure to obtain a crude product. The crude product was purified by open-column chromatography on silica gel (eluent: hexane) to quantitatively obtain 2-(1-bromo-6-(3-ethylundecan-3-yl) naphthalen-2-yl)-5-methylthiophene (compound 1-2) (0.982 g).

Example 4

Production Example (1) of Compound Represented by Formula (3)

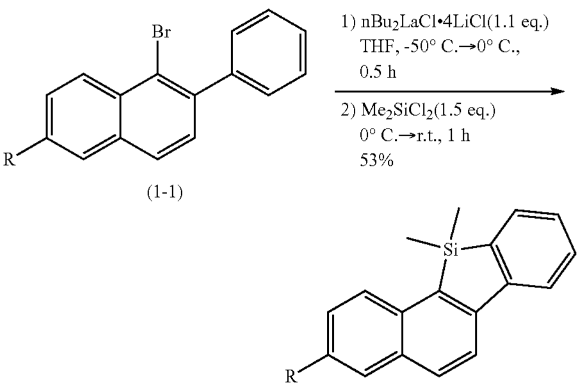

(1-1)

(3-1)

R =

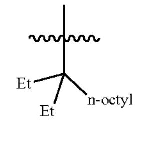

wherein nBu represents a n-butyl group; THF represents tetrahydrofuran; Me represents a methyl group; Et represents an ethyl group; and n-octyl represents a n-octyl group.

After a 0.6M hexane solution of $LaCl_3$-2LiCl (11.92 mL, 7.15 mmol) and THF (6 mL) were placed in a Schlenk tube containing a magnetic stirrer under a nitrogen atmosphere, stirring was started and the tube was cooled to −50° C. After cooling, a 1.6 M hexane solution of n-BuLi (9.0 mL, 14.3 mmol) was added dropwise at −50° C. and stirring was then performed at the same temperature for 30 minutes to prepare a lanthanide- and lithium-containing ate complex. Subsequently, compound (1-1) (3.03 g, 6.5 mmol) was added at −50° C. After the addition, stirring was continued at the same temperature for 5 minutes.

The temperature was then raised to 0° C. in 30 minutes with stirring. After dichlorodimethylsilane (1.17 mL, 9.75 mmol) was added at the same temperature, the temperature of the resulting mixture was further raised to room temperature and stirring was performed at the same temperature for 1 hour.

After completion of the reaction, water was added, and liquid separation was performed to separate an oil layer and an aqueous layer. Ethyl acetate was added to the separated aqueous layer and organic matter was extracted from the aqueous layer. This extraction operation was performed a total of 3 times. The separated oil layer and the organic layer obtained by extracting organic matter from the aqueous layer were combined and dried over $Na_2SO_4$. $Na_2SO_4$ was then filtered and the solvent was removed under reduced pressure to obtain a crude product. The crude product was purified by recrystallization to obtain 3-(3-ethyl-3-undecyl)-11,11-dimethyl-11H-benzo[b]naphtho[2,1-d]silole (compound 3-1) (1.52 g, yield: 53%).

Example 5

Production Example (2) of Compound Represented by Formula (3)

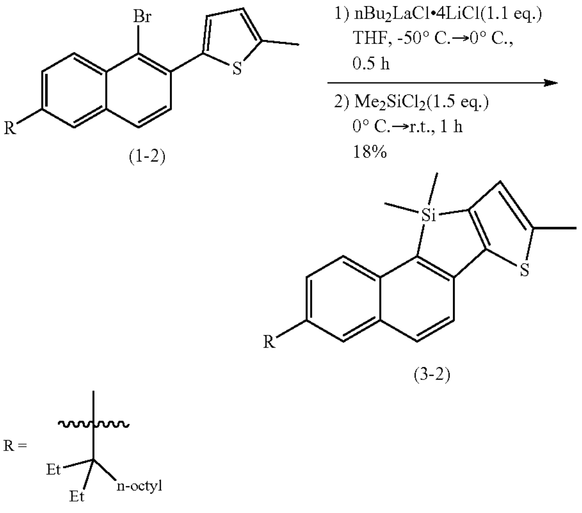

(1-2)

(3-2)

R = wherein nBu represents a n-butyl group; THF represents tetrahydrofuran; Me represents methyl; Et represents ethyl; and n-octyl represents a n-octyl group.

After a 0.6 M hexane solution of $LaCl_3$.2LiCl (1.51 mL, 0.906 mmol) and THF (0.8 mL) were placed in a Schlenk tube containing a magnetic stirrer under a nitrogen atmosphere, stirring was started, and the mixture was cooled to −50° C. After cooling, a 1.6M hexane solution of n-BuLi (1.13 mL, 1.81 mmol) was added dropwise at −50° C. and stirring was then performed at the same temperature for 30 minutes to prepare a lanthanide- and lithium-containing ate complex. Subsequently, compound (1-2) (0.40 g, 0.824 mmol) was added at −50° C. After the addition, stirring was continued at the same temperature for 5 minutes.

The temperature was then raised to 0° C. in 30 minutes with stirring. After raising the temperature, dichlorodimethylsilane (0.120 mL, 1.24 mmol) was added at the same temperature, the temperature was further raised to room temperature and stirring was continued at the same temperature for 1 hour.

After completion of the reaction, water was added, and liquid separation was performed to separate an oil layer and an aqueous layer. Ethyl acetate was added to the separated aqueous layer and organic matter was extracted from the aqueous layer. This extraction operation was performed a total of 3 times. The separated oil layer and the organic layer obtained by extracting organic matter from the aqueous layer were combined and dried over $Na_2SO_4$. $Na_2SO_4$ was then filtered and the solvent was removed under reduced pressure to obtain a crude product. The crude product was purified by open-column chromatography on silica gel (eluent: hexane) and preparative size exclusion chromatography (SEC) to obtain 3-(3-ethylundecan-3-yl)-8,10,10-trimethyl-10H-naphtho[2'1':4,5]silole[3,2-b]thiophene (compound 3-2) (69.3 mg, yield: 18%). The analytical values of the obtained compound (3-2) are as follows.

$^1H$ NMR (600 MHz, $CDCl_3$): δ 7.671 (d, J=8.4 Hz, 1H), δ 7.646 (s, 1H), δ 7.565 (d, J=9.0 Hz, 1H), δ 7.4703 (dd, J=4.5 Hz, J=1.8 Hz 1H), δ 6.829 (s, 1H), δ 2.554 (s, 3H) δ 0.545 (s, 6H) HRMS (FAB+) m/z=462.

Example 6

Production Example (3) of Compound Represented by Formula (3)

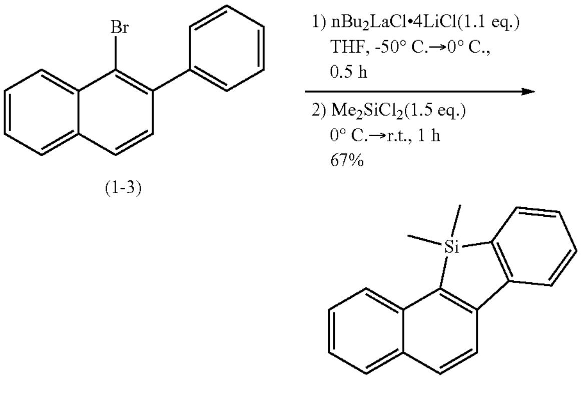

(1-3)

(3-3)

wherein nBu represents a n-butyl group; THF represents tetrahydrofuran; and Me represents a methyl group.

After a 0.6M hexane solution of $LaCl_3$.2LiCl (48 mL, 28.8 mmol) and THF (30 mL) were placed in a Schlenk tube containing a magnetic stirrer under a nitrogen atmosphere, stirring was started and the resulting mixture was cooled to −50° C. After cooling, a 1.6M hexane solution of n-BuLi (36 mL, 57.6 mmol) was added dropwise at −50° C. and the resulting mixture as stirred at the same temperature for 30 minutes to prepare a lanthanide- and lithium-containing ate complex. Subsequently, compound (1-3) (7.5 g, 26.5 mmol) was added at −50° C. After the addition, stirring was continued at the same temperature for 5 minutes.

The temperature was then raised to 0° C. in 30 minutes with stirring. After dichlorodimethylsilane (5.1 mL, 34.5 mmol) was added at the same temperature, the temperature was further raised to room temperature and the resulting mixture was stirred at the same temperature for 1 hour.

After completion of the reaction, water was added, and liquid separation was performed to separate an oil layer and an aqueous layer. Toluene was added to the separated aqueous layer and organic matter was extracted from the aqueous layer. This extraction operation was performed a total of 3 times. The separated oil layer and the organic layer obtained by extracting organic matter from the aqueous layer were combined and dried over $Na_2SO_4$. $Na_2SO_4$ was then filtered and the solvent was removed under reduced pressure to obtain a crude product. The crude product was purified by recrystallization to obtain 11,11-dimethyl-11H-benzo[b]naphtho[2,1-d]silole (compound 3-3) (4.65 g, yield: 67.4%).

Example 7

Production Example of GNR Having a Heteroaromatic Ring

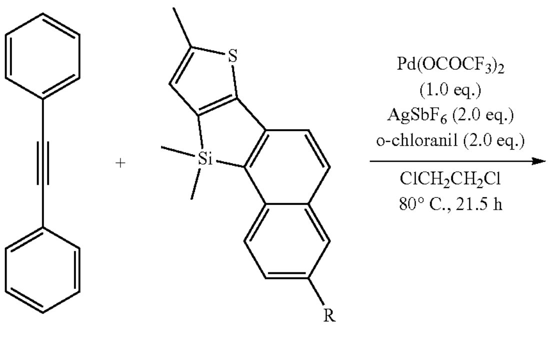

initiator I (3-2)

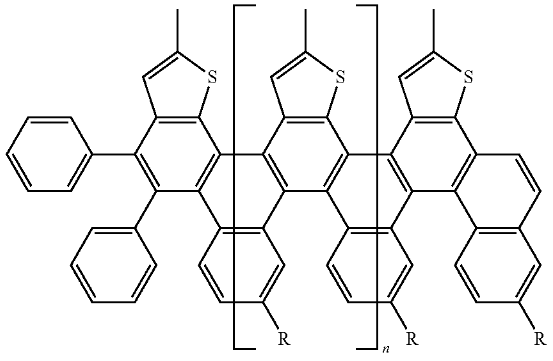

GNR1

R =
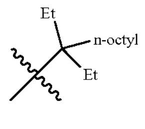

wherein Et represents an ethyl group; and n-octyl represents a n-octyl group.

The monomer (compound (3-2)) (29.4 mg, 63.5 μmol), $AgSbF_6$ (43.7 mg, 127 μmol), $Pd(OCOCF_3)_2$ (21.1 mg, 63.5 μmol), and o-chloranil (31.2 mg, 127 μmol) were placed in a 5-mL Schlenk tube containing a magnetic stirrer under a nitrogen atmosphere, and stirring was started. Initiator I (diphenylacetylene) (0.11 mg, 0.635 μmol) dissolved in 1,2-dichloroethane (0.1 mL) was then added. Subsequently, the walls of the Schlenk tube were washed with 1,2-dichloroethane (0.57 mL). The temperature was then raised to 80° C. and the reaction mixture was stirred at the same temperature for 21.5 hours to obtain a reaction mixture.

The obtained reaction mixture was cooled to room temperature and the resulting reaction mixture was passed through a silica gel short pad column and a metal scavenger (metal-trapping agent) while washing with $CH_2Cl_2$. The solvent was then removed from the reaction mixture under reduced pressure to obtain GNR1.

The obtained GNR1 was analyzed by size exclusion chromatography (SEC). The analysis showed that Mn=2.9×$10^4$ and Mw/Mn (PDI)=1.14.

Example 8

Production Example (3) of Compound Represented by Formula (1)

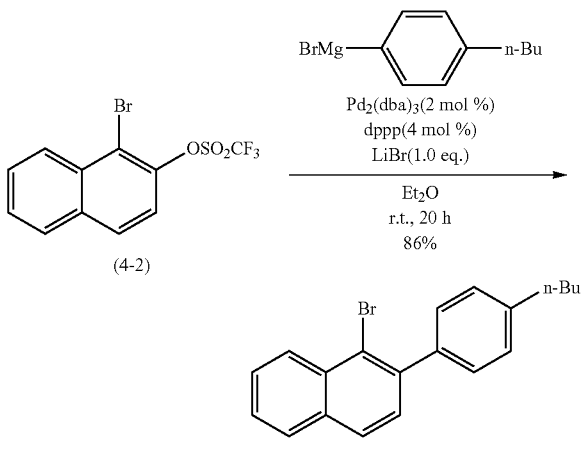

(4-2)

(1-4)

wherein dba represents dibenzylideneacetone; dppp represents 1,3-bis(diphenylphosphino)propane; Et represents an ethyl group; and n-Bu represents a n-butyl group.

Compound (4-2) (7.54 g, 14.0 mmol), $Pd_2(dba)_3$ (231 mg, 0.28 mmol), dppp (231 mg, 0.56 mmol), LiBr (1.22 g, 14.0 mmol), and $Et_2O$ (12 mL) were placed in a 100-ml two-necked round-bottom flask containing a magnetic stirrer under a nitrogen atmosphere, and stirring was started. Then, after cooling to 0° C., 4-butylphenylmagnesium bromide (3.0M in $Et_2O$, 7.01 mL) was added dropwise with stirring at the same temperature. The temperature was raised to room temperature and the mixture was further stirred at the same temperature for 20 hours, then quenched with 1M HCl, and extracted with ethyl acetate (20 mL) 3 times. The combined organic layers were washed with brine and then dried over $Na_2SO_4$. $Na_2SO_4$ was then filtered and the solvent was removed under reduced pressure to obtain a crude product.

The crude product was purified by open-column chromatography on silica gel (eluent: hexane/ethyl acetate=20:1) to obtain 1-bromo-2-(4-butylphenyl)naphthalene (compound 1-4) as a pale yellow oil (4.08 g, yield: 86%). The analytical values of the obtained compound (1-4) are as follows.

$^{1}$H NMR (400 MHz, $CDCl_3$): δ 8.41 (d, J=8.7 Hz, 1H), 7.86 (d, J=8.7 Hz, 1H), 7.83 (d, J=8.7 Hz, 1H), 7.65-7.60 (m, 1H), 7.56-7.51 (m, 1H), 7.43 (d, J=8.7 Hz, 1H), 7.39 (d, J=8.7 Hz, 2H), 7.28 (d, J=8.7 Hz, 2H), 2.71 (t, J=7.8 Hz, 2H), 1.69 (quin, J=7.8 Hz, 2H), 1.46 (sext, J=7.8 Hz, 2H), 0.96 (t, J=7.8 Hz, 3H).

$^{13}$C NMR (100 MHz, $CDCl_3$): δ 142.2, 140.7, 139.5, 133.5, 132.5, 129.5 (2C), 128.7, 128.04, 127.98 (2C), 127.92, 127.6, 127.4, 126.4, 122.5, 35.5, 33.5, 22.5, 14.0.

Example 9

Production Example (4) of Compound Represented by Formula (3)

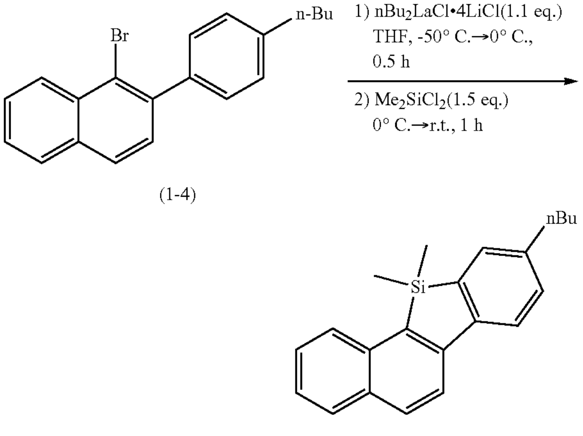

(1-4)

(3-4)

wherein nBu represents a n-butyl group; THF represents tetrahydrofuran; and Me represents a methyl group.

After a 0.6 M hexane solution of $LaCl_3$.2LiCl (27.0 mL, 16.2 mmol) and THF (30 mL) were placed in a Schlenk tube containing a magnetic stirrer, stirring was started and the resulting mixture was cooled to −50° C. After cooling, a 1.6 M hexane solution of n-BuLi (20.3 mL, 32.4 mmol) was added dropwise at −50° C. and stirring was then performed at the same temperature for 30 minutes to prepare a lanthanide- and lithium-containing ate complex. Subsequently, compound (1-4) (5.0 g, 14.7 mmol) was added at −50° C. After the addition, stirring was continued at the same temperature for 5 minutes.

The temperature was then raised to 0° C. in 30 minutes with stirring, and dichlorodimethylsilane (2.69 mL, 22.11 mmol) was added at the same temperature. The temperature was then further raised to room temperature and the resulting mixture was stirred at the same temperature for 1 hour.

After completion of the reaction, water was added, and liquid separation was performed to separate an oil layer and an aqueous layer. Toluene was added to the separated aqueous layer and organic matter was extracted from the aqueous layer. This extraction operation was performed a total of 3 times. The separated oil layer and the organic layer obtained by extracting organic matter from the aqueous layer were combined and dried over $Na_2SO_4$. $Na_2SO_4$ was then filtered and the solvent was removed under reduced pressure to obtain a crude product. The crude product was purified by recrystallization to obtain 9-butyl-11,11-dimethyl-11H-benzo[b]naphtho[2,1-d]silole (compound 3-4) (3.09 g, yield: 66%). The analytical values of the obtained compound (3-4) are as follows.

$^{1}$H-NMR (400 MHz, $CDCl_3$) δ 7.95 (d, J=8.7 Hz, 1H), 7.91 (d, J=8.7 Hz, 1H), 7.87-7.82 (m, 2H), 7.80 (d, J=7.8 Hz, 1H), 7.53-7.47 (m, 2H), 7.46-7.40 m, 1H), 7.28 (dd, J=1.8, 7.8 Hz, 1H), 2.68 (t, J=7.3 Hz, 2H), 1.71-1.62 (m, 2H), 1.42 (sext, J=7.3 Hz, 2H), 0.97 (t, J=7.3 Hz, 3H), 0.58 (s, 6H).

$^{13}$C-NMR (100 MHz, $CDCl_3$) δ 146.9, 145.7, 142.1, 139.2, 136.8, 136.5, 132.84, 132.81, 130.8, 130.3, 128.9, 128.3, 126.5, 125.2, 120.8, 119.7, 35.6, 33.8, 22.5, 14.0, −2.7 (2C).

The invention claimed is:

1. A method for producing a compound represented by formula (3):

(3)

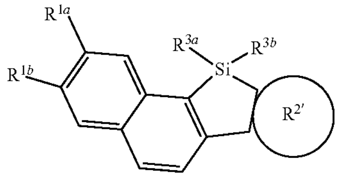

wherein $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ are optionally bound to each other to form a ring; $R^{2'}$ represents an aromatic hydrocarbon ring or a heterocyclic ring; $R^{3a}$ and $R^{3b}$ are the same or different and represent an optionally branched $C_1$-$C_4$ alkyl group or a phenyl group;

the method comprising the following steps in this order:

a step of reacting a compound represented by formula (1):

(1)

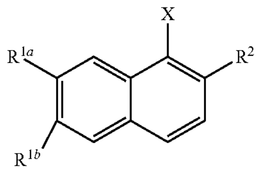

wherein $R^{1a}$ and $R^{1b}$ are as defined above; $R^2$ represents an aromatic hydrocarbon group or a heterocyclic group; and X represents a bromine atom or an iodine atom with a lanthanide- and lithium-containing ate complex to produce a lanthanide complex of the compound represented by formula (1); and a step of reacting the lanthanide complex with a silyl compound represented by formula (2):

$$R^{3a}R^{3b}SiCl_2 \quad (2)$$

wherein $R^{3a}$ and $R^{3b}$ are as defined above.

2. A graphene nanoribbon comprising at least one structural unit represented by formula (6):

(6)

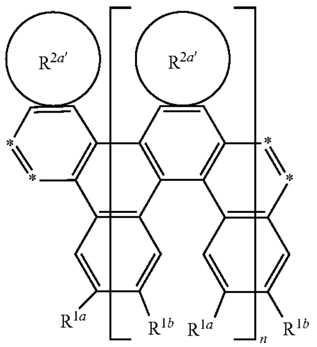

wherein * represents a bonding point; n represents an integer from 1 to 99; $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^{1a}$ and $R^{1b}$ bound to the same benzene ring are optionally bound to each other to form a ring; and $R^{2a'}$ represents a heteroaromatic ring.

3. The graphene nanoribbon according to claim 2 comprising at least one structural unit represented by formula (7):

(7)

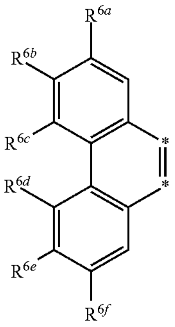

wherein the dotted line represents no bond or a single bond; * represents a bonding point; $R^{6a}$, $R^{6b}$, $R^{6c}$, $R^{6d}$, $R^{6e}$, and $R^{6f}$ are the same or different and represent a hydrogen atom, a halogen atom, an alkyl group, a cycloalkyl group, a (poly) ether group, an ester group, a boronic acid group or an ester group of boronic acid, an aromatic hydrocarbon group, or a heterocyclic group; and $R^{6c}$ and $R^{6d}$ are optionally bound to each other to form a ring.

4. The graphene nanoribbon according to claim 3 comprising at least one structural unit represented by formula (8):

(1)

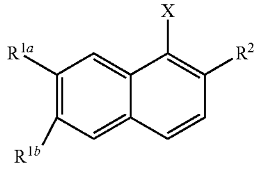

wherein the dotted lines are the same or different and represent no bond or a single bond; *1 represents a bonding point; *2 represents a bonding point when the dotted line connecting to *2 is a single bond; n represents an integer from 1 to 99; $R^{1a}$ and $R^{1b}$ are the same or different and represent a hydrogen atom, an alkyl group, a cycloalkyl group, a (poly)ether group, an ester group, a halogen atom, an aromatic hydrocarbon group, or a heterocyclic group; $R^1$a and $R^1$b bound to the same benzene ring are optionally bound to each other to form a ring; $R^{2a'}$ represents a heteroaromatic ring; $R^{6a}$, $R^{6b}$, $R^{6c}$, $R^{6d}$, $R^{6e}$, and $R^{6f}$ are the same or different and represent a hydrogen atom, a halogen atom, an alkyl group, a cycloalkyl group, a (poly)ether group, an ester group, a boronic acid group or an ester group of boronic acid, an aromatic hydrocarbon group, or a heterocyclic group; and $R^{6c}$ and $R^{6d}$ are optionally bound to each other to form a ring.

* * * * *